(12) United States Patent
Inaba et al.

(10) Patent No.: US 8,246,806 B2
(45) Date of Patent: Aug. 21, 2012

(54) MULTI-CAPILLARY ARRAY ELECTROPHORESIS DEVICE

(75) Inventors: Ryoji Inaba, Hitachinaka (JP);
 Tomohiro Shoji, Hitachinaka (JP);
 Shozo Kasai, Hitachinaka (JP); Masaya Kojima, Mito (JP); Yasushi Shimizu, Hitachinaka (JP); Seiichi Ugai, Hitachinaka (JP); Eric S. Nordman, Palo Alto, CA (US)

(73) Assignees: Applera Corporation, Norwalk, CT (US); Hitachi, Ltd., Tokyo (JP)

( * ) Notice: Subject to any disclaimer, the term of this patent is extended or adjusted under 35 U.S.C. 154(b) by 1163 days.

(21) Appl. No.: 11/714,222

(22) Filed: Mar. 6, 2007

(65) Prior Publication Data

US 2007/0158195 A1 Jul. 12, 2007

Related U.S. Application Data

(62) Division of application No. 10/259,492, filed on Sep. 30, 2002, now Pat. No. 7,250,098.

(60) Provisional application No. 60/414,090, filed on Sep. 27, 2002.

(30) Foreign Application Priority Data

Sep. 28, 2001 (JP) ................................. 2001-298987
May 31, 2002 (JP) ................................. 2002-158494

(51) Int. Cl.
 *G01N 27/453* (2006.01)
(52) U.S. Cl. ......... 204/603; 204/452; 356/344; 356/440
(58) Field of Classification Search .................. 204/452, 204/603; 356/344, 410, 411, 440
 See application file for complete search history.

(56) References Cited

U.S. PATENT DOCUMENTS

| 4,576,477 | A | | 3/1986 | Corbet et al. |
| 4,742,218 | A | * | 5/1988 | Nakamura et al. ......... 250/201.5 |
| 4,762,413 | A | * | 8/1988 | Namba et al. ................. 356/339 |
| 5,021,646 | A | | 6/1991 | Weinberger et al. |
| 5,092,973 | A | | 3/1992 | Zare et al. |
| 5,184,192 | A | | 2/1993 | Gilby et al. |
| 5,194,915 | A | | 3/1993 | Gilby |

(Continued)

FOREIGN PATENT DOCUMENTS

CA 2166830 7/1996

(Continued)

OTHER PUBLICATIONS

A. Hanning et al., "A liquid core waveguide fluorescence detector for multicapillary electrophoresis applied to DNA sequencing in a 91-capillary array," Electrophoresis, Jan. 1, 2000, vol. 21, pp. 3290-3304.

(Continued)

*Primary Examiner* — Kaj K Olsen
(74) *Attorney, Agent, or Firm* — Dickstein Shapiro LLP

(57) ABSTRACT

An electrophoresis apparatus includes a multi-capillary array having a liquid or solid disposed between the capillaries of the array. The liquid or solid exhibits a refractive index higher than that of air and less than that of water and reduces the amount of laser beams scattered by the capillaries. Also provided are methods of adjusting refracted and reflected excitation light beams passing through capillaries of a multi-capillary array, to reduce loss of intensity of the laser beams and increase irradiation of respective samples disposed in the capillaries.

10 Claims, 23 Drawing Sheets

U.S. PATENT DOCUMENTS

| | | | |
|---|---|---|---|
| 5,235,409 A | 8/1993 | Burgi et al. | |
| 5,240,585 A | 8/1993 | Young et al. | |
| 5,262,675 A | 11/1993 | Bausman, Jr. | |
| 5,312,535 A | 5/1994 | Waska et al. | |
| 5,324,401 A | 6/1994 | Yeung et al. | |
| 5,423,513 A | 6/1995 | Chervet et al. | |
| 5,430,541 A * | 7/1995 | Sapp et al. | 356/246 |
| 5,439,578 A | 8/1995 | Dovichi et al. | |
| 5,498,324 A | 3/1996 | Yeung et al. | |
| 5,516,409 A | 5/1996 | Kambara | |
| 5,552,322 A | 9/1996 | Nemoto et al. | |
| 5,567,294 A | 10/1996 | Dovichi et al. | |
| 5,570,447 A | 10/1996 | Liu | |
| 5,582,705 A | 12/1996 | Yeung et al. | |
| 5,584,982 A | 12/1996 | Dovichi et al. | |
| 5,636,017 A | 6/1997 | Bruno et al. | |
| 5,674,743 A | 10/1997 | Ulmer | |
| 5,741,412 A | 4/1998 | Dovichi et al. | |
| 5,757,014 A | 5/1998 | Bruno et al. | |
| 5,790,727 A | 8/1998 | Dhadwal et al. | |
| 5,833,827 A | 11/1998 | Anazawa et al. | |
| 5,867,266 A | 2/1999 | Craighead | |
| 5,885,430 A | 3/1999 | Kernan et al. | |
| 5,917,606 A | 6/1999 | Kaltenbach | |
| 5,938,908 A | 8/1999 | Anazawa et al. | |
| 5,993,634 A | 11/1999 | Simpson et al. | |
| 6,017,434 A | 1/2000 | Simpson et al. | |
| 6,100,973 A | 8/2000 | Lawandy | |
| 6,108,083 A | 8/2000 | Mächler | |
| 6,136,611 A | 10/2000 | Saaski et al. | |
| 6,188,813 B1 | 2/2001 | Dourdeville et al. | |
| 6,296,810 B1 | 10/2001 | Ulmer | |
| 6,304,365 B1 | 10/2001 | Whitehead | |
| 2001/0040094 A1 | 11/2001 | Inaba et al. | |

FOREIGN PATENT DOCUMENTS

| | | |
|---|---|---|
| EP | 0 476 248 A1 | 3/1992 |
| EP | 0 619 483 A1 | 10/1994 |
| GB | 2 312 505 A | 10/1997 |
| JP | 8-136502 | 5/1996 |
| JP | 09043197 | 2/1997 |
| JP | 09096623 | 4/1997 |
| JP | 09152418 | 6/1997 |
| JP | 2001-324472 | 11/2001 |
| WO | WO 94/04892 A1 | 3/1994 |
| WO | WO 96/36872 | 11/1996 |
| WO | WO 00/48023 A1 | 8/2000 |
| WO | WO 01/40764 A2 | 6/2001 |

OTHER PUBLICATIONS

T. Anazawa et al., "Capillary Array Gel Electrophoresis Using Simultaneous On-Column Detection Method for DNA Analysis," Central Research Laboratory, Hitachi, Ltd., pp. 57-58.

A. Herr et al., "Investigation of a Miniaturized Capillary Isoelectric Focusing (cIEF) System Using a Full-Field Detection Approach" Mechanical Engineering Department, Stanford University, Stanford, CA.

A. Bruno et al., "On-Column Laser-Based Refractive Index Detector for Capillary Electrophoresis," CIBA-GEIGY Ltd., Analytical Research, Anal. Chem. 1991, 63, pp. 2689-2697.

Y. Kurosu et al., "Fluorescence Detection with an Immersed Flow Cell in Capillary Electrophoresis," J. High Resolution, Mar. 14, 1991, pp. 186-190.

A. Karger et al., "Multiwavelength Fluorescence Detection for DNA Sequencing Using Capillary Electrophoresis," Nucleic Acids Research, vol. 19, No. 18, Jul. 29, 1991, pp. 4955-4962.

A. Kostichka et al., "High Speed Automated DNA Sequencing in Ultrathin Slab Gels," Bio/Technology, vol. 10, Jan. 1992, pp. 78-81.

S. Takahashi et al., "Multiple Sheath-Flow Gel Capillary-Array Electrophoresis for Multicolor Fluorescent DNA Detection," Central Research Laboratory, Hitachi Ltd., Analytical Chemistry, vol. 66, No. 7, Apr. 1, 1994, pp. 1021-1026.

R. Tomisaki et al., "High-Speed DNA Sequencer Using Capillary Gel Electrophoresis with a Laser-Induced Four-Color Fluorescent DNA Detector," Dept. of Chemistry, Kobe Pharmaceutical University, The International Journal of the Japan Society for Analytical Chemistry, vol. 10, No. 5, Nov. 16, 1994, pp. 817-820.

Q. Li, "Laser-Based Detection System for High-Throughput DNA Sequencing with Multiplexed Capillary Electrophoresis," Iowa State University, Ames, Iowa, Apr. 1996, pp. 1-293.

X. Lu et al., "Optimization of Excitation and Detection Geometry for Multiplexed Capillary Array Electrophoresis of DNA Fragments," Iowa State University, Applied Spectroscopy, vol. 49, No. 5, May 1995, pp. 605-609.

T. Anazawa et al., "A Capillary-Array Electrophoresis System Using Side-Entry On-Column Laser Irradiation Combined with Glass Rod Lenses," Electrophoresis 1999, 20, pp. 539-546.

* cited by examiner

FIG. 1a
FIG. 1b
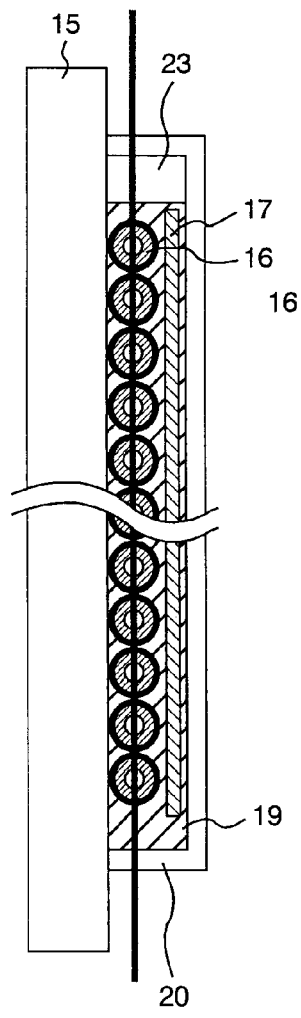
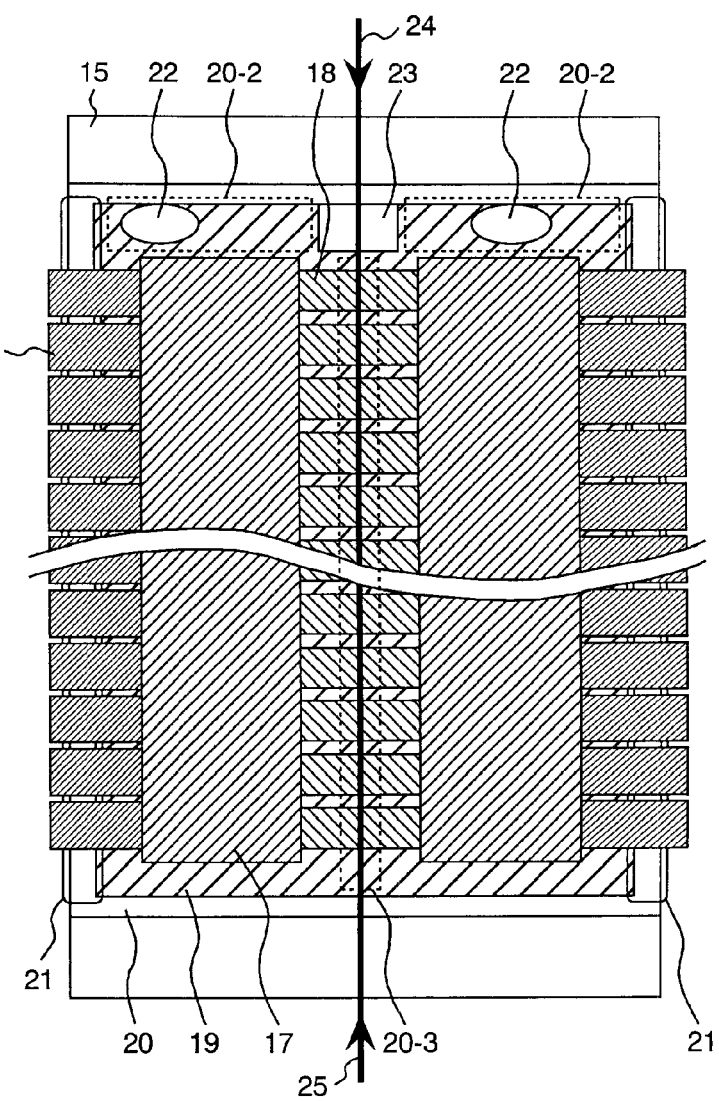

FIG. 3a
FIG. 3b
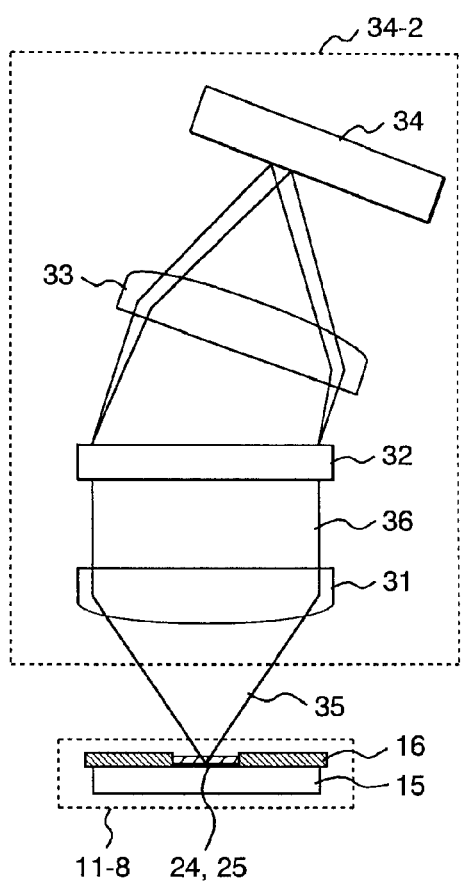
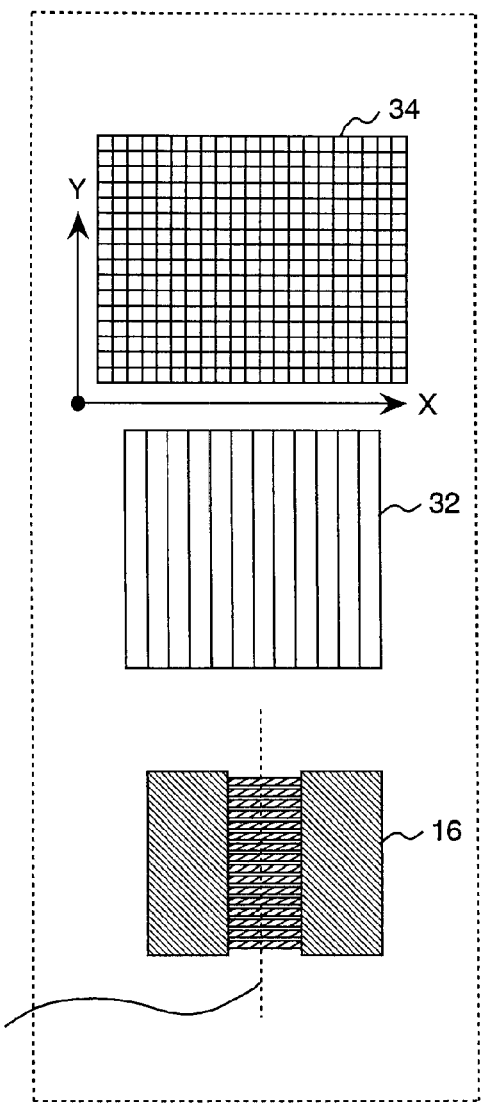

DETECTION OF FLUORESCENT LIGHT

FIG. 14a
FIG. 14b
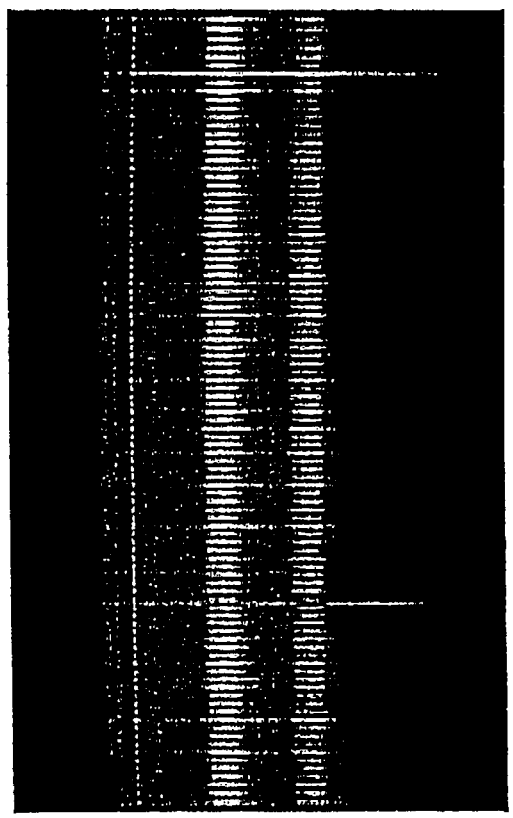
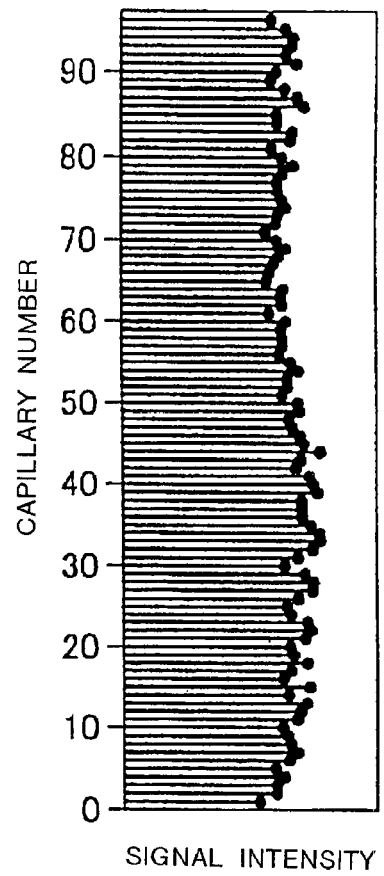

FIG. 19a
FIG. 19b
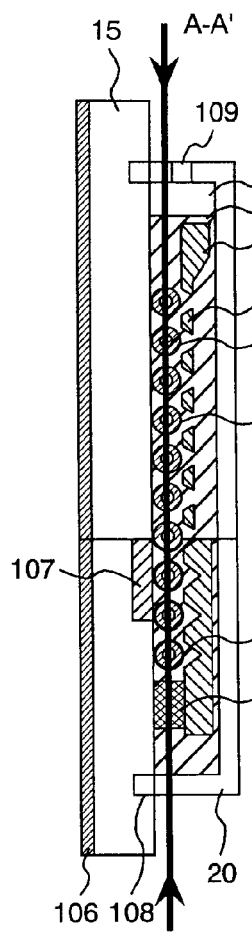
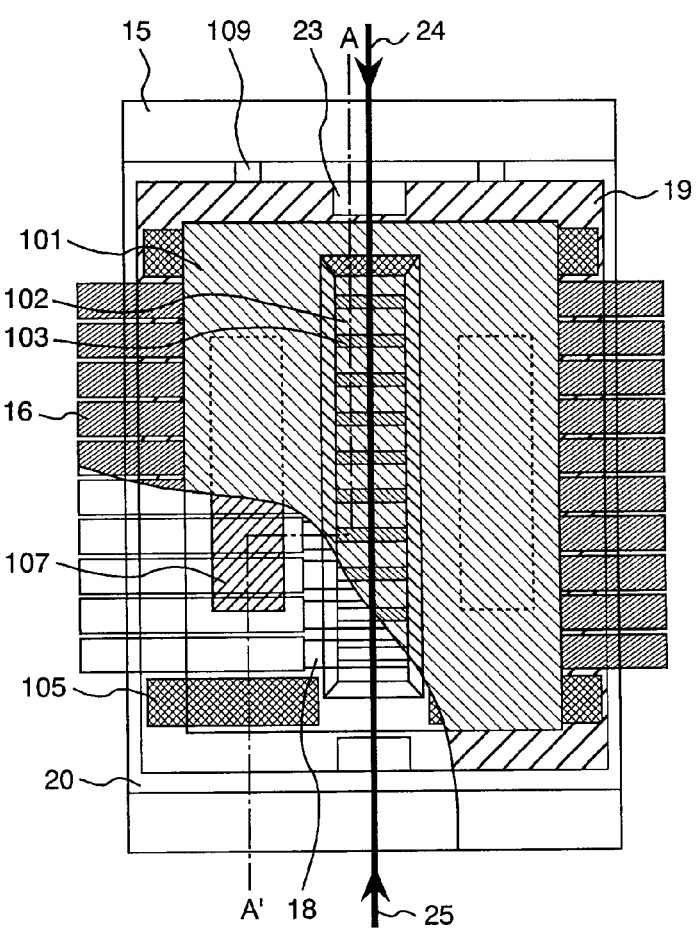

FIG. 21

| | |
|---|---|
| APPEARANCE | CLEAR, COLOR LESS |
| AVERAGE MOLECULAR WEIGHT | 670 |
| BOILING POINT (1ATM) | 174 °C |
| POUR POINT | -50 °C |
| ESTIMATED CRITICAL TEMPERATURE | 567 K |
| ESTIMATED CRITICAL PRESSURE | $1.13 \times 10^6$ PASCALS |
| VAPOR PRESSURE | 192 PASCALS |
| LATENT HEAT OF VAPORIZATION (AT NORMAL BOILING POINT) | 70 J/g |
| LIQUID DENSITY | 1860 kg/m$^3$ |
| KINEMATIC VISCOSITY | 2.5 CENTISTOKES |
| ABSOLUTE VISCOSITY | 4.7 CENTPOISE |
| LIQUID SPECIFIC HEAT | 1100 Jkg$^{-1}$ °C$^{-1}$ |
| LIQUID THERMAL CONDUCTIVITY | 0.65 Wm$^{-1}$ °C$^{-1}$ |
| COEFFICIENT OF EXPANSION | 0.0012 °C$^{-1}$ |
| REFRACTIVE INDEX | 1.291 |
| WATER SOLUBILITY | 7 ppmw |
| SOLUBILITY IN WATER | <5 ppmw |
| OZONE DEPLETION POTENTIAL | 0 |

FIG. 22

| AF Type | $n_D$ | Abbe No.* | dn/dT ($T<T_g$), ppm/°C | dn/dT ($T>T_g$), ppm/°C |
|---|---|---|---|---|
| 1600 | 1.31 | 92 | -77 | -329 |
| 2400 | 1.29 | 113 | -78 | -378 |

*Abbe Number = $\dfrac{(n_D - 1)}{(n_F - n_C)}$

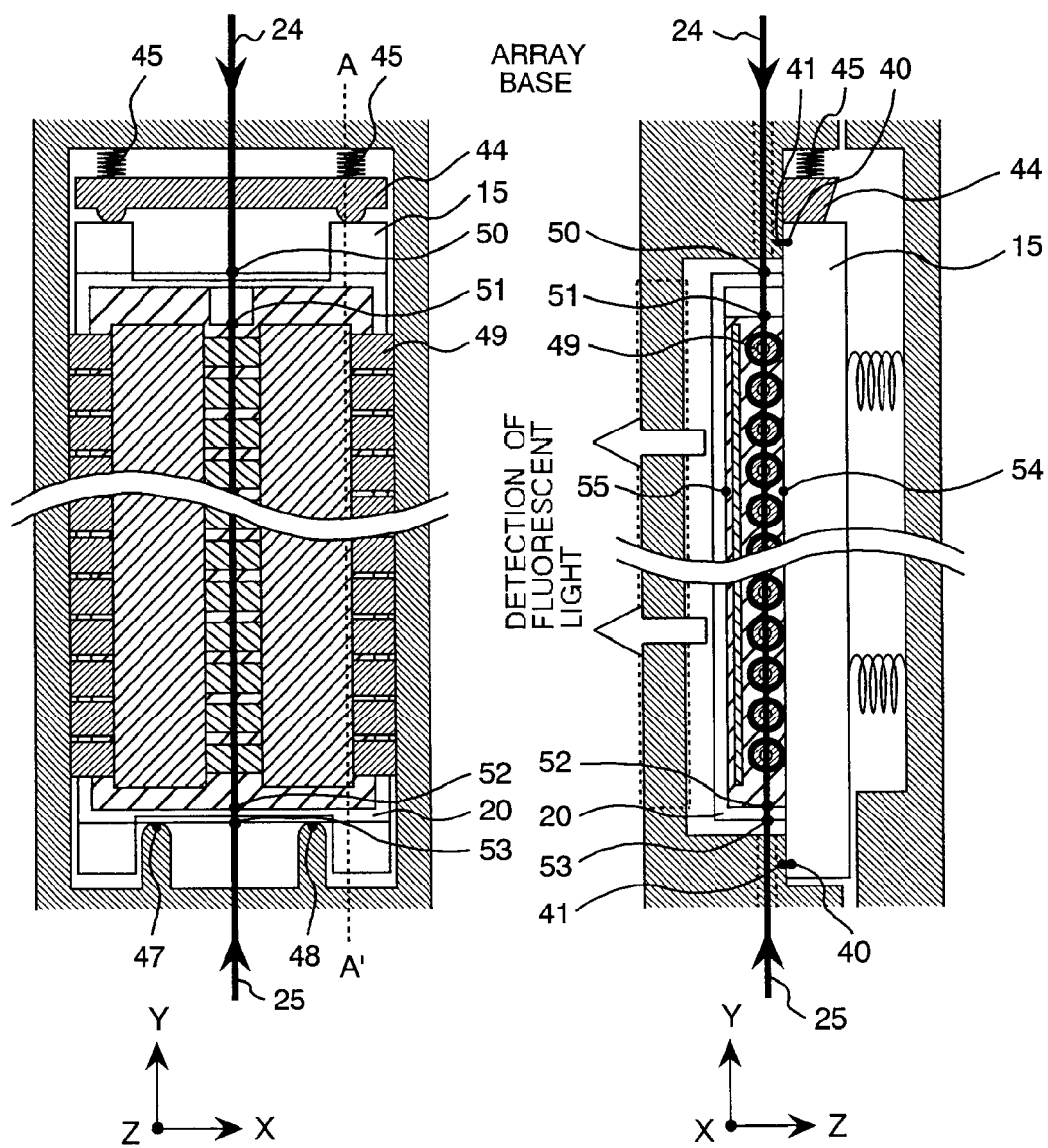

MULTI-CAPILLARY ARRAY ELECTROPHORESIS DEVICE

CROSS REFERENCE TO RELATED APPLICATIONS

The present application is a divisional of U.S. application Ser. No. 10/259,492, filed on Sep. 30, 2002, now U.S. Pat. No. 7,250,098, which in turn claims priority benefit from Japanese Patent Applications Nos. 2001-298987, filed Sep. 28, 2001, and 2002-158494, filed May 31, 2002, and claims the benefit of earlier filed U.S. Provisional Patent Application No. 60/414,090, filed Sep. 27, 2002 in the name of Nordman et al., and entitled "Multi-Capillary Array Electrophoresis Device", all of which are herein incorporated in their entireties by reference.

FIELD

The present application relates to an electrophoresis apparatus for separating a sample, such as DNA labeled with a fluorescent substance, through electrophoresis, and for analyzing the sample.

BACKGROUND

To determine the DNA base sequence and base length, electrophoresis method using a capillary comprising a fused silica tube and its polymer covering is utilized. A sample including the DNA to be measured is put into the separation medium such as polyacrylamide in the fused silica capillary, and voltage is applied across the capillary.

The DNA compound in the sample migrates in the capillary and is separated according to the molecular weight to produce a DNA band in the capillary. Each DNA band is provided with fluorescence dye, which emits light in response to laser beam. This is read by the fluorescence measuring apparatus to determine the DNA sequence. The same technique is employed for separation and assaying of a protein to examine the configuration.

According to a laser-irradiated method, a laser beam is directed toward the capillary on the end of one or both sides of the capillary array. The capillary array can consist of multiple capillaries arranged on a plane substrate. The aforementioned laser beam is transmitted to the adjacent capillaries one after another across the capillary array. On or around the region of the capillary exposed to laser beam, protective coverings such as polyimide coverings on the surface of the capillary, can be removed. However, if laser beams pass through the boundary between surfaces having different refractive indices, e.g. the contact surface between the capillary and air, then the laser light will be damped by divergence and reflection of the laser light, for example, due to differences in refractive indices of the substances constituting the boundary. Consequently, in the process where laser light is transmitted through several capillaries, laser light decays exponentially, resulting in deterioration of precision in assaying.

SUMMARY

To reduce loss of the laser beam due to refraction and reflection, a light transfer medium having a predetermined refractive index is filled around capillaries. Aspects of techniques that can be advantageously adapted according to various embodiments include aspect described in U.S. Pat. Nos. 5,790,727; 5,582,705; and 5,833,827; and in Japanese Laid-Open Patent Publication Nos. Hei 09-152418 and 09-96623, all of which are incorporated herein in their entireties by reference.

According to various embodiments, improvements in assaying precision of an electrophoresis apparatus are provided wherein a laser beam can be directed along a beam path to irradiate respective irradiatable portions of respective capillaries of a multi-capillary array. The improvements include provisions that ensure the simultaneous irradiation of multiple capillaries of the array, for example, the simultaneous irradiation of all the capillaries of the array.

Various embodiments provide an electrophoresis apparatus wherein laser beam is directed along a beam path toward a detection zone that includes respective irradiatable portions of the capillaries of the array. The array contains multiple capillaries that allow a sample to be separated by electrophoresis. The laser beam is directed along a beam path that ensures the simultaneous irradiation of an irradiatable portion of each capillary of the array, in the detection zone. The laser beam can pass through multiple capillaries, and fluorescence information about the samples migrating through the capillaries can be detected.

The electrophoresis apparatus can be characterized according to various embodiments by including a liquid or solid having a refractive index greater than that of air and smaller than that of water, and provided in the space or region around the capillaries of the array. The liquid or solid can reduce the amount of the laser beam that is scattered by the capillaries and lost. The liquid or solid can be disposed around, surrounding, and/or between the capillaries of a multi-capillary array. It is to be understood that the term between refers not only to the area or volume between two capillaries separated from one another, but also to the area or volume between two capillaries that are in contact with each other.

According to various embodiments, the configuration can adjust the refraction and reflection of the laser beam passing through capillaries. The adjustment can be used to reduce the loss of light caused by passing the light through many capillaries, and can avoid or minimize a reduction in the intensity of light used to illuminate or excite a sample.

According to various embodiments, a substance can be disposed around the capillaries, and can be a liquid, semi-solid, or solid at room temperature and under standard atmospheric pressure. The refractive index of the substance can be lower than that of water. The substance to be filled around capillaries can have at least the same refractive index as that of water, or lower. Further, the substance can have a refractive index greater than that of air or vacuum, for example, greater than 1. Exemplary substances that can be used for this purpose include fluorine-containing compounds that can be liquid, semi-solid, or polymeric in form at room temperature and under normal atmospheric pressure. Exemplary substances can have refractive indices of from about 1.25 to about 1.32. Other suitable fluorine-containing compounds are discussed in more detail below.

Various embodiments provide an electrophoresis apparatus wherein the aforementioned multiple capillaries can be immersed in a liquid. Such an apparatus can be constructed with one or more feature that accommodates the expansion of the liquid due to a rise in the temperature of the liquid, thereby avoiding damage of the vessel or liquid leakage. The temperature of the liquid can be controlled to adjust the gradient of refractive index of the liquid at the site or area through which the laser beam passes, whereby bending of the laser beam can be prevented or minimized to preserve the intensity of excitation light directed at the sample in each capillary.

According to various embodiments, an electrophoresis apparatus is provided wherein a transparent medium having a predetermined refractive index is provided around the capillaries, surrounding the capillaries, or between the capillaries of a multi-capillary array. The direction of light beams emitted from the sample, also referred to herein as emission beams, can be adjusted by forming the transparent medium with a curved surface. The curved surface can be used to direct emission beams toward a detector and to improve the intensity of emission beams to be detected.

BRIEF DESCRIPTION OF THE DRAWINGS

FIG. 1 includes a front view and side view of a portion of an electrophoretic apparatus according to various embodiments, including the irradiatable portions of the capillaries of the multi-capillary array of embodiment 1 discussed below;

FIG. 3 includes schematic views of a detection system according to various embodiments for detecting fluorescent light emitted from a multi-capillary array;

FIG. 6 includes parts 6a and 6b. Part 6a is a front view of a capillary array mounting section according to embodiment 2 described below. Part 6b is a cross-sectional view taken along line A-A' in part 6a;

FIG. 14 has a part 14a that shows the image formed on the CCD obtained from the apparatus of embodiment 1 described below, and a part 14b that shows the distribution of the intensity of emissions from 96 capillaries and corresponds to the CCD image shown in part 14a;

FIG. 19 includes parts 19a and 19b. Part 19a is a front view of a portion of an electrophoretic apparatus according to various embodiments, including the irradiatable portions of the capillaries of the multi-capillary array of embodiment 11 discussed below. Part 19b is a cross-sectional view taken along line A-A' in part 19a;

FIG. 21 is a table representing the chemical properties of F solution;

FIG. 22 is a drawing representing the refractive index of the F polymer;

FIG. 23 includes parts 23a and 23b. Part 23a is a front view of an electrophoretic apparatus according to various embodiments showing details of a multi-capillary array attachment part. Part 23b is a cross-sectional view taken along line A-A' in part 23a.

DETAILED DESCRIPTION OF CERTAIN EMBODIMENTS

Embodiment 1

Figure 2:
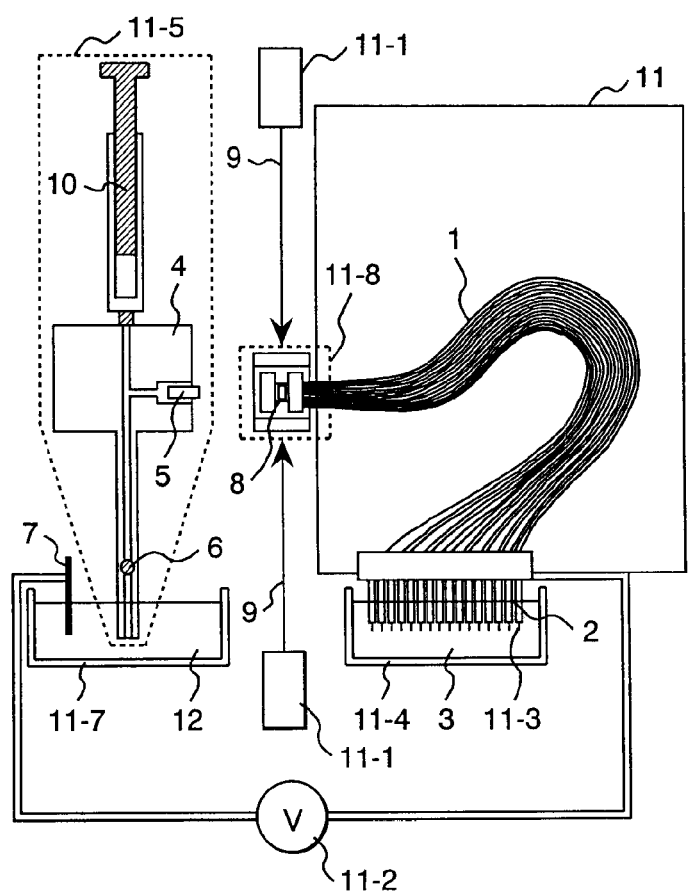
FIG. 2 is a schematic external view representing a multi-capillary electrophoresis apparatus according to the various embodiments.

FIG. 2 is a drawing representing the overall configuration of a multi-capillary electrophoresis apparatus according to various embodiments. The multi-capillary electrophoresis apparatus can comprise a multi-capillary array 1 consisting of multiple capillaries. Each capillary can contain a separation medium for separating a sample to be tested. The apparatus can also include a first buffer vessel 11-4 for holding the buffer 3 such that a negative electrode 2 of the multi-capillary array, and a sample introduction part 11-3, can be immersed. The apparatus can include a gel block comprising a valve 6, and a second buffer 11-7 for holding the buffer 12 and wherein the gel block 4 and a ground electrode 7 can be immersed. The apparatus can include: a syringe 10 for supplying a gel as a medium for electrophoresis in the capillary array; a measuring part 11-8 for obtaining information on the sample; a light source 11-1 for applying a light source such as a laser beam 9 as a coherent light to the irradiatable portions of the capillaries; a measuring part (not illustrated) for measuring fluorescent light emitted from the respective samples; an oven with air-circulation 11 for adjusting the temperature of capillary array; and a high voltage power source 11-2 for applying voltage to the separation medium.

The multi-capillary array 1 can contain 96 fused silica capillaries as tubular members filled with aqueous polymer solution as a separation medium for separating fragments of a DNA molecule in a sample to be tested. A sample introduction part 11-3 can be provided for introducing the sample into the capillary. The part 11-3 can be formed on one end of the multi-capillary array 1 where an electrode 2 for applying negative voltage can be arranged. On the other end of the array a connection part 5 can be provided connected with the gel block 4 to allow injection of the separation medium from the gel block 4 to the multi-capillary array 1.

The measuring part 11-8 including the irradiatable portions 8 that are to be exposed to excitation light can be located between the sample introduction part 11-3 and connection part 5.

The gel block 4 and syringe 10 form a fluid medium injection part 11-5 for injecting aqueous polymer solution as a separation medium into the capillary. When the aqueous polymer solution as a separation medium is injected into the capillary, the valve 6 can be closed and the syringe 10 can be inserted into position, whereby the aqueous polymer solution can be injected into the capillary. The multi-capillary array 1, gel block 4, buffer 3, electrode 2, buffer 12, ground electrode 7 and high voltage power source 11-2 constitute a voltage application part for electrophoresing the sample under test. At the time of electrophoresis, the negative electrode 2 can be immersed in the buffer 3 and the valve 6 can be opened. This establishes a conducting path consisting of the negative electrode 2, buffer 3, multi-capillary array 1 including the aqueous polymer solutions in the capillaries, gel block 4 including aqueous polymer solution in the gel block, buffer 12, and ground electrode 7. Voltage can be supplied to this conducting path from the high voltage power source 11-2. When voltage is applied to the conducting path, the sample under test in aqueous polymer solution starts to migrate and is separated in conformity to the properties such as molecular weight.

The air-circulating oven 11 is a temperature control part for controlling the temperature of the capillary array. This allows the greater part of the capillary array 1 to be kept at a constant temperature (e.g. at 60° C.).

The optical system of the electrophoresis apparatus comprises the light source 11-1, the measuring part 11-8 containing the irradiatable region 8, and the measuring or detecting part for detecting the fluorescent light emitted from the irradiatable portions of the capillaries. The light source 11-1 can generate a laser beam 9 (488.0 nm and 514.5 nm beams emitted from an argon ion laser) as coherent light.

The excitation light laser beam 9 is directed toward the irradiatable region 8. The capillaries of the array can be arranged parallel and adjacent to one another in a plane in the measuring part 11-8. Excitation light such as laser beam 9 can be applied to or directed at the measuring part 11-8 from two directions—upward and downward directions—in order to ensure simultaneous excitation through irradiation parts 8 of multiple capillaries. The excitation light laser beam 9 can excite a sample being tested, to cause fluorescent light to be emitted from the sample. Various embodiments provide information about the sample, such as a nucleic acid base sequence.

FIG. 3*a* shows a detection mechanism 34-2 and measuring part 8. The detection mechanism 34-2 can comprise or can consist of a fluorescent light collimating lens 31, a grating 32, a focus lens 33, and a CCD 34. Fluorescent light 35 emitted from samples contained in the respective capillaries and irradiated with excitation light, is converted into parallel beams or rays of light by the fluorescent light collimating lens 31. The collimated light is then split spatially by the grating 32 and an image is formed on the CCD 34 by the focusing lens 33. Optics for image formation are depicted in the FIG. 3*b* schematically. Ninety-six capillary images are arranged in the Y-axis direction, and light emitted from each capillary is dispersed in the X-axis direction.

The following describes the measuring part 11-8: FIG. 1 contains a side view (1*a*) and front view (1*b*) of the measuring part 11-8. The measuring part 11-8 consists of 96 capillaries 16, array base 15, cell cover 20, holding plate 17, bubble eliminating block 23, filled medium (F solution 19) and bubble 22.

The following describes the capillary array structure: A reference plane surface for placing the capillary is formed on the array base 15. To ensure that all 96 capillaries are kept in contact with the reference plane surface and adjacent capillaries are kept in contact with each other, they are arranged on the array base 15.

The capillaries 1 can be bonded to the array base 15 and are fixed in position by being inserted between the holding plate 17 for fixing the capillaries 1 and the array base 15. This allows the capillaries to be arranged in parallel on the plane surface, and the variation in the distance of the center axis of each capillary from the plane surface is kept at 6 μm or smaller. Consequently, this will reduce the influence due to the loss of laser beam 9 resulting from diffusion and reflection when laser beam 9 is irradiated so as to propagate successively to the adjacent capillary across 96 capillaries.

The following describes the capillary configuration: Each capillary 16 can be configured in such a way that the fused silica tube 18 can have, for example, an inner diameter of about 50 μm and an outer diameter of 126 μm that can be covered with a 12-μm thick polymer coating. The overall outer diameter can measure, for example, 150 μm. The capillary can be filled with aqueous polymer solution (having a refractive index of about 1.41, for example) as a DNA separation medium.

In the region of each capillary tube that includes a light irradiatable part 8, also referred to herein as an irradiatable portion, to which excitation light is directed, the polymer coating can be removed to expose the underlying fused silica 18 of the capillary. When excitation light, for example, laser beams 9, are directed to the irradiatable parts 8, part of the irregularly reflected light contacts the polymer coating of the capillary and the polymer coating can emit fluorescent light in some cases. However, the fluorescent light from this polymer coating can be blocked by the holding plate 17, and prevented from reaching the detection mechanism. This ensures high sensitivity detection characterized by a high signal to noise ratio.

According to various embodiments, a sealed structure can be formed by the array base 15 and a fused silica-made cell cover 20 by bonding together with an adhesive 21, thereby providing a sealed cell for holding a transparent medium such as specific liquid and/or solid. Filling this cell with transparent medium ensures that the space through which excitation light passes between the capillaries is filled with the transparent medium. In other words, the irradiatable parts 8 of the capillaries 1 can be immersed in the transparent medium. Since the high voltage is applied to the capillary during electrophoresis, the capillary attracts the dust particles in charged air. However, since the portions of the capillaries including the irradiatable portions are separated from the outside by the sealed cell, the irradiatable parts 8 do not attract and hold dust particles.

Selection of the aforementioned transparent medium has a serious impact on the analysis capability in the assaying of electrophoresis. To explain this, the following describes the problems with the propagation and loss of laser beam. According to various embodiments, laser beam s 24 and 25 are directed so that they will overlap with each other. Each of laser beams propagates successively to the adjacent capillaries one after another, across 96 capillaries to traverse the irradiation part 8 of the capillary. Here when the laser beams 24 and 25 travel across the boundary between the capillaries 16 and the transparent medium, laser beams 24 and 25 have to pass through the boundary between the media having different refractive indices, with the result that light intensity will be lost due to scattering of the laser beam caused by refraction and reflection. When light intensity of laser beam s 24 and 25 is weakened by this loss, fluorescent light emitted from samples in the capillaries 16 will be reduced, so highly sensitive analysis of DNA sequence and others will be difficult to achieve.

To solve the problem of the loss of laser beams, fluorescent light can be increased by raising the laser beam intensity. However, if the intensity of the laser beam is excessive, the test sample such as a DNA molecule or the like will be denatured. In this sense, this method is restrictive. Further, in an electrophoresis apparatus where a laser beam passes through multiple capillaries, a problem is found in the difference of the intensities of laser beams reaching and irradiating each of the different capillaries. As the laser beam passes through the capillaries, the intensity is decreased exponentially due to refraction and reflection. A large difference occurs between the fluorescent light emitted from the capillary where the incoming laser beam intensity is the strongest and that from the capillary that is the weakest (the capillaries located at the center when laser beams are used to irradiated a multi-capillary array from both sides). In this case, the detection range of the CCD 34 must be set in such a way that all the fluorescent light can be accommodated. So if there is a large difference in the intensity of fluorescent light, the analysis performance of the CCD 34 cannot be effectively utilized, with the result that analysis performance will be deteriorated. For this reason, if there is a large difference in the intensity of laser beams from one capillary to another, the samples in the capillaries cannot be analyzed effectively. The loss due to retraction and reflection is increased exponentially as the number of capillaries in which laser beam propagates is increased. In an electrophoresis apparatus comprising about 24 or more capillaries, a significant problem can be the loss in the intensity of excitation light due to refraction and reflection. Loss caused by refraction and that caused by reflection depend on the difference in the refractive index on the boundary. If there is a significant difference in the refractive indices of the two sides of the boundary, (if the reflection factor is significant), attenuation can be caused by reflection when the excitation light passes through the boundary. If the difference in the refractive indices is small, attenuation can be caused by divergence of the excitation light, or laser beams, when the light passes through the boundary. To solve this problem according to various embodiments, the present inventors have found out it is effective to reduce the total loss due to refraction and reflection by filling the space between capillaries with a medium having a predetermined refractive index.

The following describes the loss due to reflection: The following formula is generally used to obtain the reflection factor (R) when light propagates at an incident angle of 0 from medium 1 (refractive rate: n1) to medium 2 (refractive index: n2):

Reflectance: $R=\{(n1-n2)/(n1+n2)\}^2$

For example, when air is used to fill around the capillaries, reflection factor on the boundary between air (n=1.00) and fused silica (n=1.46) is 3.49%. So every time laser beam passes through one boundary, beam of 3.49% is reflected, with the result that light intensity will be lost. This loss is increased exponentially with the increase in the number of capillaries passed by laser beam. To reduce the loss caused by reflection, the refractive index of the filling medium should be made closer to that of the capillary.

Further, the loss caused by refraction is the attenuation resulting from diffusion of laser beam passing through the boundary. In other words, when the capillary has a cross section shaped in an ellipse or a circle, the boundary between the capillary and filling medium will act as a converging lens Because the index of refraction of the separation medium (n=1.41) is less than that of the fused silica capillaries (n=1.46), the lumen of the capillary will act as a diverging lens. The capillary inner diameter is smaller than the capillary outer diameter so the diverging lens effect is for the same index of refraction difference.

If the capillary and its medium have a small refractive index difference, the lens effect of the boundary will be reduced, and the laser beam is diverged to cause loss. Generally, the following formula is used to obtain the relationship between incoming angle è1 and outgoing angle è2 when light has launched from medium 1 (refractive rate: n1) to medium 2 (refractive index:n2):

$n1 \sin è1 = n2 \sin è2$

For this reason, to increase the lens effect of the capillary and to reduce the loss due to refraction, it is generally necessary to increase the difference in refractive index between the filling medium and capillary. Based on this way of thinking, various embodiments involve using a simulated relationship between the refractive index N of the transparent medium around the capillary, and emission intensity ratio. This simulation was made using a multi-capillary array having 96 capillaries equipped with the same structure of the irradiatable part as that of the present embodiment, wherein the capillary was filled with aqueous polymer solution having a refractive index of 1.41, and laser beams were directed at both sides of the capillary array. The variation in distance from capillary center axis to the plane surface was ±6 μm, and the laser diameter was 72 μm, with the misalignment of optical axis assumed at 10 μm.

Figure 13:
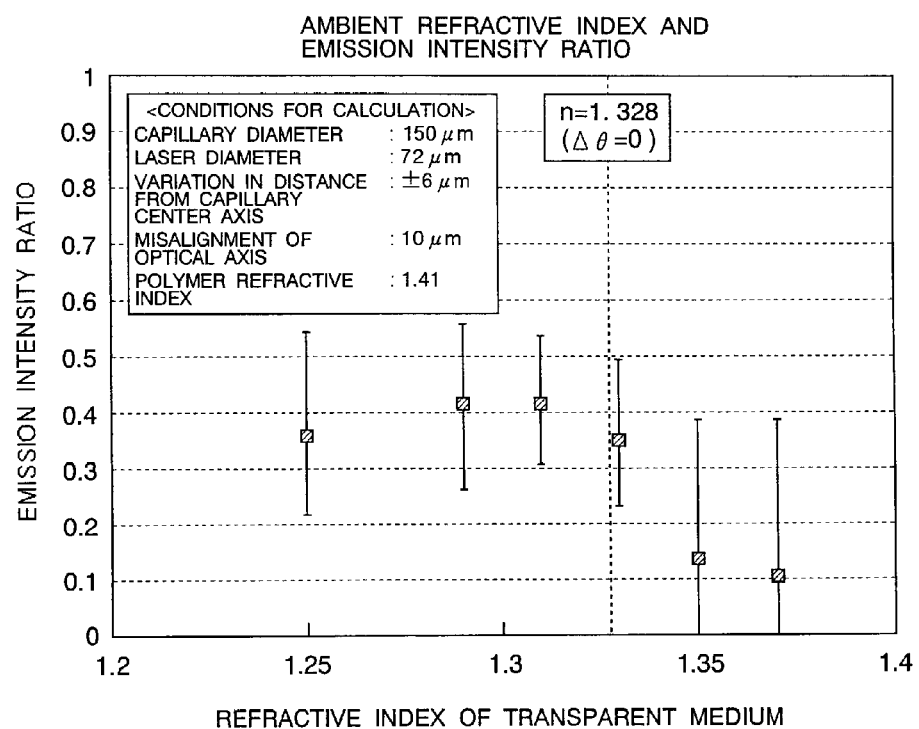
FIG. 13 shows the result of simulating the refractive index and emission intensity ratio of a filling medium.

FIG. 13 shows the result of this simulation. The horizontal axis indicates the refractive index of the transparent medium, and the vertical axis shows the intensity of laser beam which passes through the inside of each capillary averaged for 96 capillaries relative to the intensity of incident laser beam. The intensity had a serious impact on the analysis performance of the CCD as means for detecting fluorescence of the test sample. The boxes in the middle of the vertical lines on the graph indicate the expected values of the emission intensity ratio. The lines in the vertical direction including the boxes show the distribution of the emission intensity. It can be seen that the emission intensity ratio is shaped like a cone whose apex is formed by the refractive index of about 1.29, with respect to the refractive index of the filling medium. When the refractive index is smaller than 1.29, the loss caused by reflection is greater. When refractive index is 20 larger than 1.29, the loss caused by refraction is greater. If the emission intensity ratio is 0.35 or greater, it can be seen that the transparent medium around the capillaries is preferred to have a refractive index from 1.25 to 1.32. The transparent medium having a refractive index of 1.29 can be used.

A transparent medium can be selected that does not absorb excitation light, for example, laser beams. This is to reduce the attenuation of light intensity when laser beam passes through the transparent medium. This attenuation will increase if there are a greater number of capillaries and the laser beam path in the transparent medium is longer. Further, a transparent medium can be selected that does not emit fluorescent light. If the transparent medium emits fluorescent light due to exposure to the excitation light, the fluorescent light will create noise and create background which reduces the dynamic range with the result that the performance of the analysis will be deteriorated.

According to various embodiments, the transparent medium can be Fluorinert Electronic Liquid FC-43 (hereinafter abbreviated as "F solution 19"), where "Fluorinert" is a registered trademark of 3M, Inc.

The F solution 19 is a fluorinated liquid having a refractive index of about 1.29, and a low viscosity. It is colorless, transparent, and very stable in thermochemical properties. It does not absorb laser beams. Even when exposed to laser beams, it emits fluorescent light having an intensity equivalent to, or less than, the Raman scattering of water. Accordingly, this provides a very suitable material for the medium of a multi-capillary array electrophoresis apparatus. Further, it has the following characteristics, which are included in transparent medium according to various embodiments (1) excellent electric insulation and thermal conductivity, (2) very small surface tension and superb permeability, (3) insolubility in solvents whether temperature is high or low, (4) non-combustibility and free of poison and odor, and (5) an inactivity without corroding electronic parts, metal, plastic, or rubber.

FIG. 21 shows the chemical properties of F solution at 25° C. The sealed vessel of the multi-capillary array in the present embodiment is filled with F solution 19, and the irradiation part 8 is immersed in F solvent 19. This reduces the loss of intensity of the laser beams when they pass through the surface of the capillaries 16, and avoids reduction of the intensity of fluorescent light emitted from the test sample. These characteristics ensure improved analysis performance in a multi-capillary array electrophoresis apparatus having multiple capillaries, for example, having 24 or more capillaries. The sealed structure can be is filled with a bubble 22 as well as with F solution 19. This is to prevent the closed structure from being damaged by the expansion of the volume of F solution 19 resulting from temperature change. However, since the bubble 22 is made movable, it may immigrate into the laser light path to give an adverse effect to analysis. To prevent the bubble 22 from crossing the laser light path, a fused silica-made bubble-eliminating block 23 as a bubble eliminator can be formed in the sealed structure.

The bubble-eliminating block 23 can be in an upper position when the measuring part 11-8 is mounted on the electrophoresis apparatus. It is placed in the path of the laser beams 24 and 25. Then the space 20-2 for storing bubble 22 can be formed above the sealed vessel where laser beams 24 and 25 do not pass. At the time of measurement, bubble moves to the upper portion of the cell, and remains in this space 20-2, thereby preventing the bubble 22 from crossing the laser beam paths.

Further, when the irradiation part 8 is mounted on the electrophoresis apparatus so that the reference surface of the array base 15 is horizontal and capillaries are located lower than the reference surface, a groove-formed space is formed on the array base 15 close to the irradiatable part 8. The bubble tends to stay in the gap of capillaries close to the irradiation part. However, if the volume in the groove-formed space is equal to or greater than that of the bubble 23, then the bubble remains in this space, with the result that contact between the bubble 22 and laser beams 24 and 25 can be avoided.

Further, the same effect can be obtained when the irradiation part 8 is mounted oblique to the electrophoresis apparatus in such a way that the bubble 22 moves to one end of the sealed vessel where it is not exposed to the laser beams 24 and 25. In other words, when the irradiation part is mounted on the electrophoresis apparatus, the sealed structure is configured so that the staying bubble is not exposed to laser beam s 24 and 25, whereby contact between the bubble 22 and laser beams 24 and 25 can be avoided. This configuration avoids the loss due to refraction and reflection caused by laser beams passing by the boundary between the bubble and F solution 19.

Figure 4A:
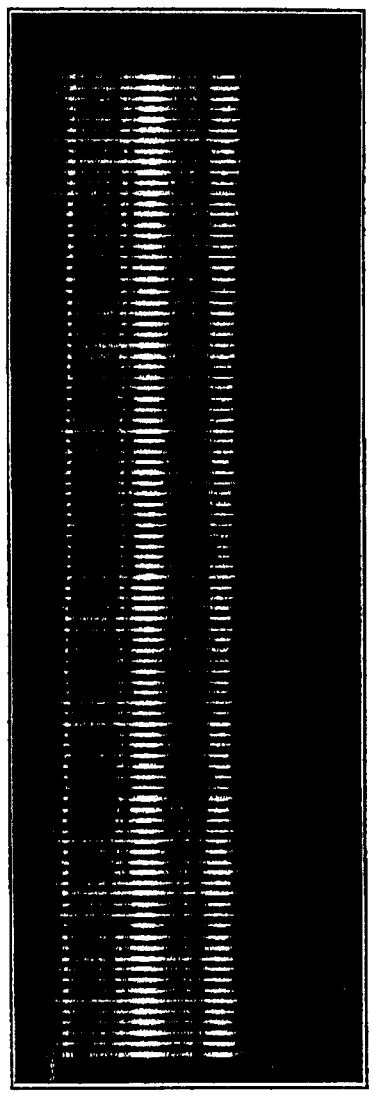
FIG. 4 shows the image formed on a CCD and obtained from experiment 1 described below, and the distribution of the intensity of emissions from 93 capillaries of a multi-capillary array.
Figure 4B:
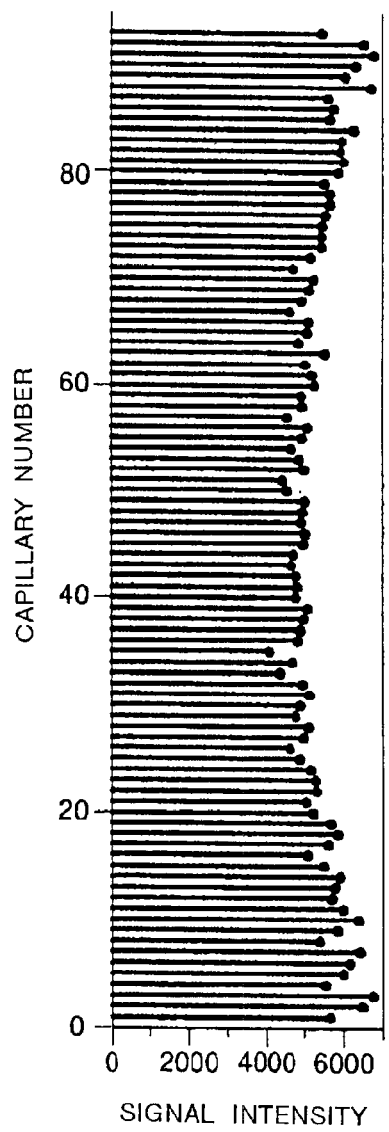

FIGS. 14a and 14b show the image formed on the CCD according to an embodiment and the distribution of the intensities of emissions from 96 capillaries. FIG. 4 shows the image formed on the CCD for 93 capillaries and the distribution of the intensities of emissions from 93 capillaries. The emissions shown in FIGS. 14a and 14b represent a spectrum (mainly the Raman scattering of water) emitted from the separation medium. As illustrated, emission from 96 capillaries can be detected at the same time.

Figure 5:
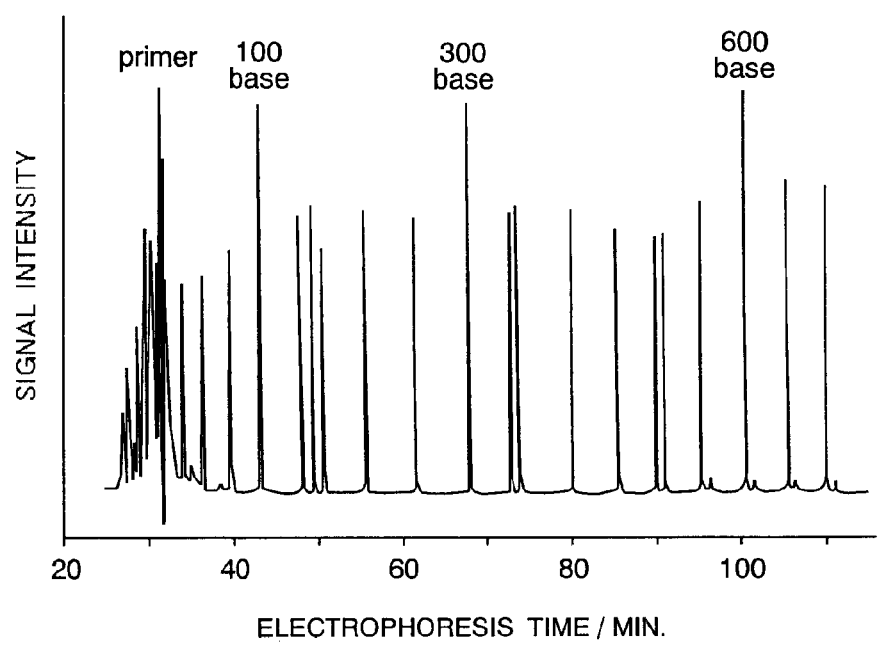
FIG. 5 shows the result of electrophoresis obtained from the apparatus of embodiment 1 described below.
Figure 15:
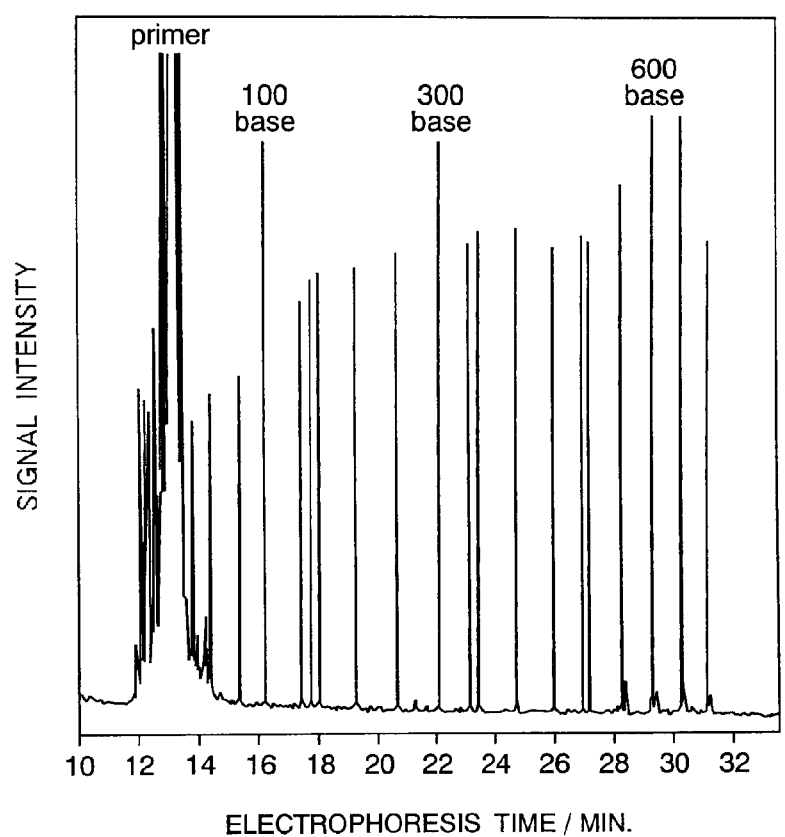
FIG. 15 shows the result of electrophoresis of one of 96 capillaries, according to an embodiment.

FIG. 15 shows the result of electrophoresis of one of 96 capillaries. FIG. 5 shows the result of electrophoresis of one of 93 capillaries. The current target of measurement is the DNA sample (so-called size maker) with its base length known. The temperature in the air-circulating oven is 60° C., and the length between the irradiation part and sample introduction terminal is 36 cm, with the average field applied to the capillary being 319 volts per centimeter. A crossover point is one of the indices for indicating the DNA separability of the electrophoresis. This means the length of a base where the separation length equivalent to one base on the irradiation part is equal to the full width at half maximum of the DNA band of one base. It shows that the greater this value, the greater the separability in electrophoresis. The crossover point in FIG. 15 has been found in 410 bases. The same result has been gained from other 95 capillaries. The crossover point in FIG. 5 has been found in 410 bases. The same result has been gained from other 92 capillaries.

As described above, various embodiments provide a multi-capillary electrophoresis apparatus of high analysis performance where the crossover point for each capacity is found in 410 bases.

Embodiment 2

The angle formed between an incoming laser beam and laser entry surface on a multi-capillary array, or cell, can be maintained constant. If this angle is different for each capillary array, the incident angle of the laser will vary, with the result that the laser light path in the cell will vary. For example, if the laser entry surface on the cell is made of fused silica, and the medium filling the cell is a liquid having a refractive index of 1.29, the displacement of the laser light path at the point where the laser beam has propagated in 20 mm from the entry point into the cell will be 20 µm if the laser entry surface of the cell varies by 4 mrad.

If laser is displaced in the axial direction of the capillary, two laser beam s irradiated in two directions (upward and downward directions) can cease to be coaxial, and the effective laser diameter can be increased, with the result that performances such as separability in DNA detection will be deteriorated. Further, if laser beam is displaced in the direction (hereinafter abbreviated as "Z-axis direction") vertical to both the capillary axis and the laser beam axis, the amount of laser beam irradiation of the inner diameter of the capillary will be reduced, and the signal intensity will decline. To avoid such deterioration in performance, it is necessary to ensure that the angle formed between incoming laser beam and laser entry surface on the cell is maintained constant.

In a multi-capillary array electrophoresis apparatus according to various embodiments, the inner diameter of the capillary filled with a separation medium and test sample is 50 µm, the tolerance of the distance of center axis of the capillary and the reference surface is ±6 µm, and the excitation light is a laser light having a diameter measuring 72 µm that can be precisely adjusted to the order of µm. Otherwise, the satisfactory sensitivity cannot be maintained. Further, the multi-capillary array can be dismountable from the electrophoresis apparatus.

When it is to be mounted, a precise and easy positioning adjustment between the capillary and laser beam can be provided. For this reason, the embodiment 2 can be configured in such a way that a constant angle maintained between the reference surface for mounting the multi-capillary array on the electrophoresis apparatus and the laser entry surface on the cell, and a constant angle can be maintained between this reference surface for mounting and that on the apparatus side at all times. The surface where multiple capillaries are arranged can be brought in contact with the mounting reference surface on the multi-capillary array mounting section of the electrophoresis apparatus, whereby adjustment can be made of the relative position between the plane substrate and the electrophoresis apparatus in the direction vertical to the aforementioned mounting reference surface. At the same time, the one plane surface in the cell which is vertical to the plane surface where capillaries are arranged and parallel to the axes of the capillaries, can be brought into contact with another mounting reference surface on the multi-capillary array mounting-section. An adjustment can thus be made of the relative position between the capillary array and the electrophoresis apparatus in the direction vertical to the aforementioned vertical direction. As such, a constant angle can be maintained between the incoming laser beam and laser entry surface of the cell.

Figure 6A:
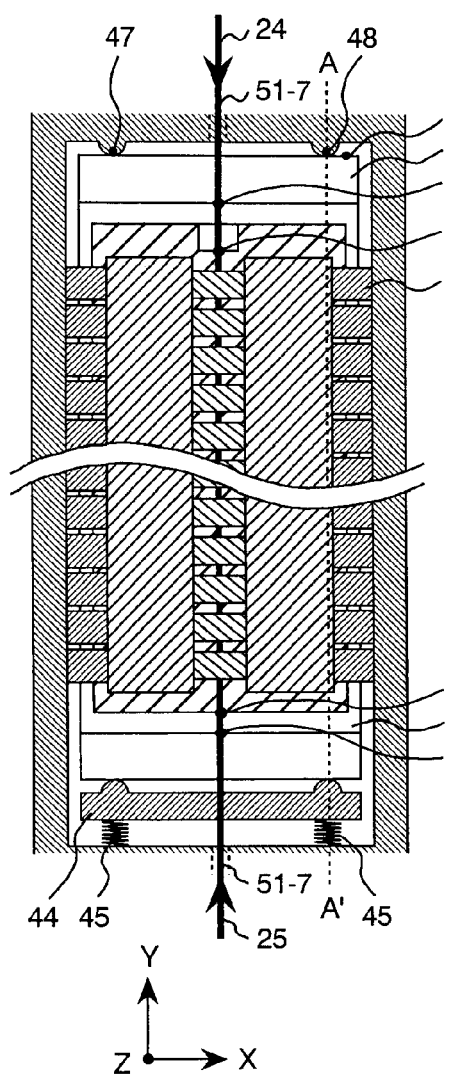
Figure 6B:
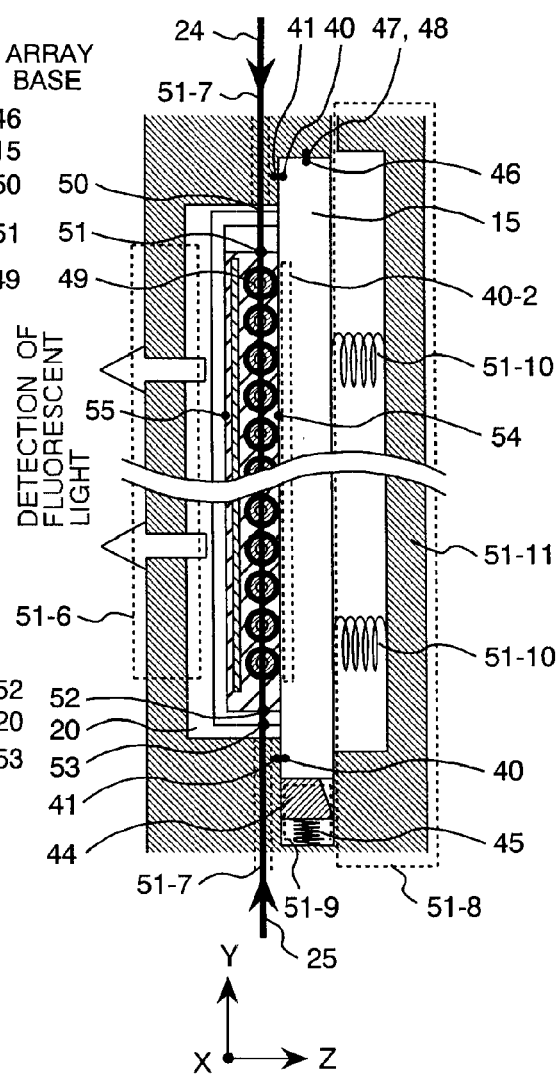

FIG. 6 shows the front view (6a) of the capillary array mounting section according to the embodiment 2 25 and a cross-sectional view taken along line A-A' of the front view shown in FIG. 6b. Others arrangements can include the same as those described in Embodiment 1 above. The X, Y and Z axes are defined as shown in the figure. The X-axis is the axis parallel to the capillary axis, and Z-axis is the axis vertical to the reference plane surface where multiple capillaries are arranged, with the Y-axis being the axis vertical to both the X- and Z-axes.

On the fused silica-made array base 15 are formed a reference plane surface 40-2 where the capillaries can be arranged through contact with the polymer coating of the capillaries, a mounting reference surface 40 in contact with the electrophoresis apparatus and a mounting reference surface 46. The mounting reference surface 46 of the array base 15 is vertical to the reference plane surface 40 and is parallel to the X-axis.

The reference plane surface 40-2 is approximately parallel to the mounting reference surface 40, and the distance between them is preferred to be 6 μm or smaller. If the reference plane surface 40-2 and mounting reference surface 40 are formed on one and same plane as in the present embodiment, the capillary array can be produced to a high precision, so this formation is preferable.

On the capillary mounting section on the electrophoresis apparatus is formed a mounting reference surface 41 and mounting reference lines 47 and 48 to which the mounting reference surface 40 of the multi-capillary array and the mounting reference surface 46 are respectively brought in contact. It contains a laser beam transmission part 51-7 passed by the laser beams 24 and 25 entering the irradiatable part 8, a fluorescent light transmission part 51-6 passed by the fluorescent light emitted from the sample, a pressure part 51-8 comprising a mounting section cover 51-11 and spring 51-10, and a pressure part 51-9 comprising a holding rod 44 and spring 45. The pressure part 51-8 can be moved when the multi-capillary array is mounted or dismounted from the capillary array base. When it is mounted, the mounting reference surface 40 is brought in contact with the mounting reference surface 41 of the multi-capillary array mounting section of the electrophoresis apparatus. The array base 15 is pressed in the −z axis direction (from the mounting reference surface 40 to mounting reference surface 41) by pressure part 51-8, whereby the relative positioning between the array base 15 and electrophoresis apparatus in the Z-axis direction can be carried out with a high degree of precision on the order of μm. This positioning ensures the reproducibility of the positions for the laser beams and the irradiatable portions when the capillary is mounted. When the reference plane surface 40-2 and the mounting reference surface 40 are located on the same plane, positional relationship between the center axis of each capillary and the path of laser beams 24 and 25 can be adjusted with an extremely high degree of precision.

When the mounting reference surface 46 of the array base 15 is brought in contact with two capillary mounting reference members semicircular as viewed from above the Z-axis, it is brought in contact with the mounting reference lines 47 and 48. The array base 15 is pressed against it in the Y-axis direction (from the mounting reference surface 46 to the mounting reference lines 47 and 48) by the spring 45 through the holding rod 44 comprising two capillary holding members semi-circular as viewed from above the Z axis. As described above, one straight line is in contact at two points as viewed from the Z-axis direction, and this enables relative positioning between the array base 15 and the electrophoresis apparatus in the Y-axis direction with a high degree of precision.

In the capillary array, capillaries are arranged so that the mounting reference surface 46 and each capillary will be parallel with each other. Further, the distance between the capillary 49 closest to the mounting reference surface 46 and the mounting reference surface 46 is made constant for any capillary array. This allows the position relationship between each capillary and the mounting reference lines 47 and 48 to be determined uniquely for the capillaries ranging from the closest capillary to all the following 95 capillaries. Accordingly, the position of imaging on the CCD 34 does not depend on the capillary array, and the light receiving surface of the CCD 34 can be minimized.

If the laser light path varies in the X-axis direction, the laser beams 24 and 25 in the two upper and lower directions ceases to be coaxial, so the laser beam diameter increases effectively. This will result in the reduction in performances such as reduction in the separability for DNA detection. If the laser beam s 24 and 25 are displaced in the Z-axis direction, there will be a reduction in the amount of laser beam irradiated inside the capillary, with the result that signal intensity is reduced. To avoid reduction in performances, surfaces 50, 51, 52 and 53 are made parallel to the surface 46, as described above. To minimize the variations of the laser light path, the angle of mounting the array base 15 on the electrophoresis apparatus should be made constant with a high degree of reproducibility. This condition can be met according to the aforementioned method of pressing the surface 46 against the lines 47 and 48.

The following describes various embodiments for mounting a multi-capillary array on a capillary array mounting section. FIG. 23 shows the front view (23a) of the capillary array mounting section as an variation of the embodiment 2 and cross sectional view taken along line A-A' in the front view of FIG. 23b. The X, Y and Z axes are defined as shown in the figure. The surface 40 of the array base 15 (surface in contact with the capillary polymer coating) is brought in contact with the mounting reference surface 41 on the array mounting section of the electrophoresis apparatus, thereby adjusting the relative position between the array base 15 and the electrophoresis apparatus in the Z-axis direction. This position adjustment has ensured the reproducibility of the position exposed to laser beam when the capillary array is mounted or remounted. Further, the array base 15 is pressed in the Y-axis direction by the spring 45 through the holding rod 44, and the surface 53 of the cell (vertical to the surface 40 and parallel to the X axis) is brought in contact with the mounting reference lines 47 and 48, thereby adjusting the relative position between the array base 15 in the Y-axis direction and the electrophoresis apparatus. Further, the capillaries of the capillary array are arranged so that the surface 53 is parallel to each capillary, and the distance between the capillary 49 closest to the surface 53 and the surface 53 is made constant for any one of the capillary arrays. As a result, the position of imaging on the CCD 34 does not depend on the capillary array, and the light receiving surface of the CCD 34 can be minimized.

All the capillaries can be aligned in a specific area of the array base, parallel to the reference surface 46. The largest and smallest distances of the edge of the specific area are predetermined for any capillary array. This structure is realized in such a way as described with reference to FIG. 8 where two parallel blocks are formed on the array base, and the area between the blocks are the specific area where 96 capillaries are aligned. In this case, it is necessary to keep constant the distances of inner wall (capillary-side wall) of the two blocks and reference surface 46 for any capillary arrays. The light receiving surface of the CCD 34 can be minimized with this configuration.

The parallelism of the surfaces 50, 51 and 52 exposed to the laser beam s 24 and 25, and surface 53, out of the surfaces of the fused silica-made cell cover 20, is made to be $2 \times 10^{-3}$ rad or smaller. If this parallelism varies for each capillary array, the incident angle of the laser beams 24 and 25 upon the cell 20, hence, the laser light path in the cell varies. If the laser light path varies in the X-axis direction, the laser beams 24 and 25 in the two upper and lower directions cease to be coaxial, so the laser beam diameter increases effectively.

This will result in the reduction in performances such as reduction in the separability for DNA detection. If the laser beam s 24 and 25 are displaced in the Z-axis direction, there will be a reduction in the amount of laser beam irradiated inside the capillary, with the result that signal intensity is reduced. To avoid reduction in performances, surfaces 50, 51 and 52 are made parallel to the surface 53, as described above.

To minimize the variations of the laser light path, it is not sufficient to ensure that the surfaces 50, 51 and 52 are parallel to the surface 53. It is also necessary to ensure that the angle of mounting the array base 15 on the electrophoresis apparatus is constant with a high degree of reproducibility. This condition can be met according to the aforementioned method of pressing the surface 53 against the lines 47 and 48.

In the method shown in FIG. 6, the cell 20 can be installed and bonded to array base 15 in such a way that the surface 50 of the cell 20 and the surface 46 of the array base 15 will be parallel to each other. According to this method, the surface 53 of the cell 20 can be brought in direct contact with the mount reference lines 47 and 48, resulting an increased margin of parallelism between the array base 15 and cell 20.

According to various embodiments, the resolution of the electrophoresis apparatus deteriorates if temperature gradient occurs to the filling medium between capillaries, and this is caused by the bending of laser beam due to gradient of the refractive index in the filler medium. According to various embodiments, a solution to problem is provided. If there is a temperature increase of the medium (F solution 19) in the Z-axis direction, the refractive index of the F solution 19 will increase in the Z-axis direction. This increase of refractive index causes the propagating direction of the laser beams 24 and 25 ideally having only the components the Y-axis direction will come to have components in the Z-axis direction although in a small amount. The direction of laser beams 24 and 25 propagating in the Y-axis direction will be displaced in the Z-axis direction by the gradient of this refractive index, causing the laser beam to deviate from the capillary array. This reduces the intensity of the laser beams applied to the capillary, hence the signal intensity (intensity of the fluorescent light emitted from the samples), resulting in a deteriorated sensitivity of the electrophoresis apparatus. This problem is more conspicuous with the increase in the distance of the laser beams 24 and 25 passing through the medium (increase in the number of capillaries). The problem can be solved by adjusting the surface temperature inside the sealed vessel, without having to use a complicated configuration. Based on this assumption, various embodiments examine the relationship between difference in the internal surface temperature and the gradient of the temperature at a predetermined position in the filling medium. The result is given in FIG. 7.

Figure 7:
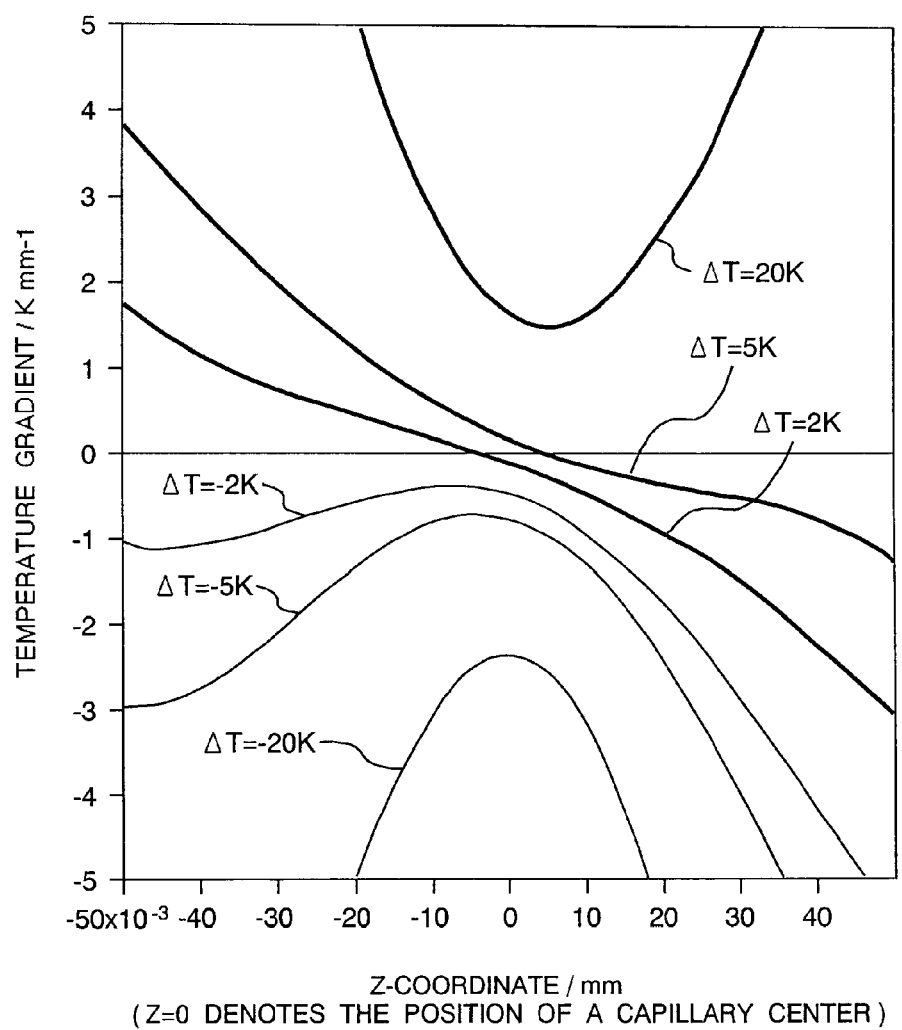
FIG. 7 shows the result of calculating the temperature gradient on line VW.

FIG. 7 shows the temperature difference between point 54 and point 55 in the array shown in FIG. 6, with the gradient of the temperature on a straight line between points 54 and 55. The horizontal axis indicates the Z-axis coordinate on the line between points 54 and 55, and Z=0 axis is equivalent to the center position of the capillary.

The line between points 54 and 55 is vertical to the array base, and passes through the center of the space between capillaries. The distance between points 54 and 55, i.e., thickness of the F solution layer, is 0.8 mm, and the vertical axis indicates the temperature gradient. T denotes the difference in temperature between point 54 and point 55 (where .T=temperature at point 54—temperature at point 55). Each curve represents the temperature gradient on line 54-55 for the F solution when .T is −20, −5K, −2K, 2K, 5K and 20K. The thermal conductivity of F solution is 0.066 W/mK, and the specific heat is 1050 J/kgK, with the density at 1880 kg/m3. Further, for calculation, heat generation for each capillary during electrophoresis is assumed to be 1 mW per 10 mm in length.

As can be seen from FIG. 7, the absolute value of temperature gradient is smaller when .T is positive (temperature at point 54 is greater than that at point 55) than when it is negative. In other words, the deviation of the temperature gradient is smaller when the temperature of the plane substrate of the array base 15 is higher than that of the cell cover 20, than the reverse case. Based on this result, the multi-capillary array has been designed as shown in FIG. 6. The multicapillary array according to the present embodiment is configured in such a way that the thickness of the fused silica-made array base 15 as a first flat plate of the sealed vessel is larger than that of the fused silica-made cell cover 20 (the thickness of the transparent plate as part of the aforementioned cell passed by the signal light from the capillary array to be detected) as a second flat plate. If the array base 15 is made of sapphire, the .T can be kept positive even if the array base 15 is thinner than the cell cover. In other words, the capillary array is designed in such a way that the thermal conduction efficiency of the first flat plate is greater than that of the second flat plate.

In this manner, when the multi-capillary array mounting section is kept at a constant temperature of e.g. 60° C., the array base 15 transmits the heat to the surfaces 40 and 41 (mounting reference surface 40 and mounting reference surface 41) more effectively than the cell cover portion in contact with the surfaces 47 and 48. The multi-capillary array mounting section can be kept at a constant temperature of, for example, 60° C., whereby .T is maintained positive. This will reduce the temperature gradient, hence refractive index gradient. This ensures straight traveling property, and improves resistance of the laser light path against bending. The multi-capillary array can be designed so that temperature gradient of the filling medium at the site passed by laser beam will be zero during electrophoresis. The temperature gradient being zero signifies that laser beam can travel straight because there is almost no temperature gradient, and sensitivity is hardly deteriorated by bending of laser beam.

The aforementioned configuration improves the resolution of an electrophoresis apparatus where the space between capillaries is filled with the filling medium.

Embodiment 3

The embodiment 3 characterized in that the medium uses Teflon AF 2400 of Dupont (hereinafter abbreviated as "F polymer") as a fluorinated polymer having a refractive index of 1.29 or Teflon AF 1600 of Dupont (hereinafter abbreviated as "F' polymer") as a fluorinated polymer having a refractive index of 1.32. Here "Teflon" is a registered trademark of the Dupont product.

Figure 8A:
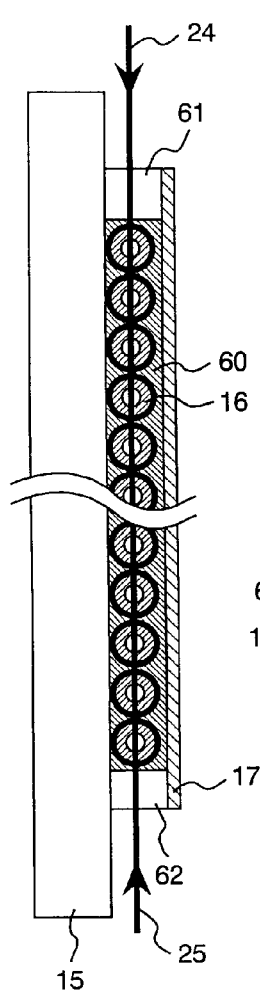
FIG. 8 shows a side view and front view of a portion of an electrophoretic apparatus according to various embodiments, including the irradiatable portions of the capillaries of the multi-capillary array of embodiment 3 discussed below.
Figure 8B:
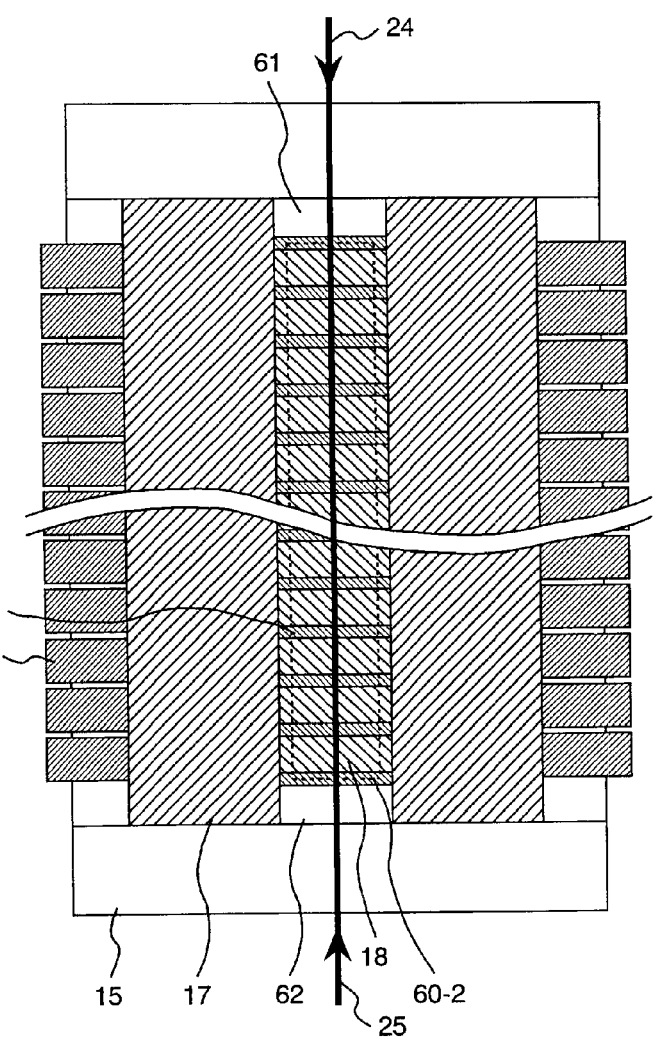

FIGS. 8a and 8b show a side view (8a) and front view (8b) of a portion of the apparatus of embodiment 3 including the irradiatable portions of the capillaries. Configurations other than the irradiatable part 8 are the same as that of embodiment 1. Further, it is also possible to use the medium containing the recurring unit that has at least one of the following chemical structures A, B, C and D. They are characterized in that all the hydrogen atoms have been replaced by fluorine atoms. Similarly to the aforementioned F solution, they can be used as excellent transparent mediums.

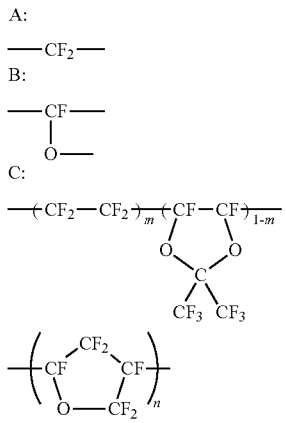

The irradiation parts 8 of the capillary array 1 are formed on the array base 15. They are arranged on the array base 15 and are bonded and fixed to the array base 15 together with the holding plate 17 in order to ensure that the capillaries on the array base 15 will contact the array base 15 and the adjacent capillaries. This configuration uniquely determines the positional relationship between each capillary and mounting reference surface, similarly to embodiment 2.

The capillaries 16 can be covered with a thin polymer film, similarly to the case in embodiment 2. In the irradiatable part 60-2, the polymer coating is removed and the fused silica tube 18 is exposed to the outside. In the invention according to the embodiment 3, the irradiatable part 60-2 where the fused silica tube 18 is exposed to the outside is covered with the F polymer as a fluorinated polymer having a refractive index of 1.29. It can also be covered by Teflon AF 1600 of Dupont (a registered trade mark) (hereinafter abbreviated as "F' polymer") as a fluorinated polymer having a refractive index of 1.32.

After the capillary 16 has been fixed to the array base 15, the space between capillaries is filled with F polymer 60. The polymer 60 has been filled in such a way that the laser light paths 24 and 25 are completely covered in the space between two polymer blocks 61 and 62 located at the outer positions on both ends. The following shows a chemical formula E for the F polymer, where "n" is a natural number.

E:

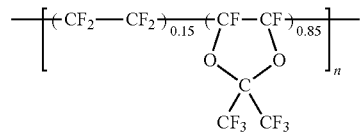

Further, the F polymer and F' polymer are characterized as follows:
(1) High temperature stability, (2) Excellent chemical resistance, (3) Low surface energy, (4) Low water absorption, (5) Transparency and superb light transmission, (6) Very low refractive index, and (7) high gas permeability.

Figure 20:
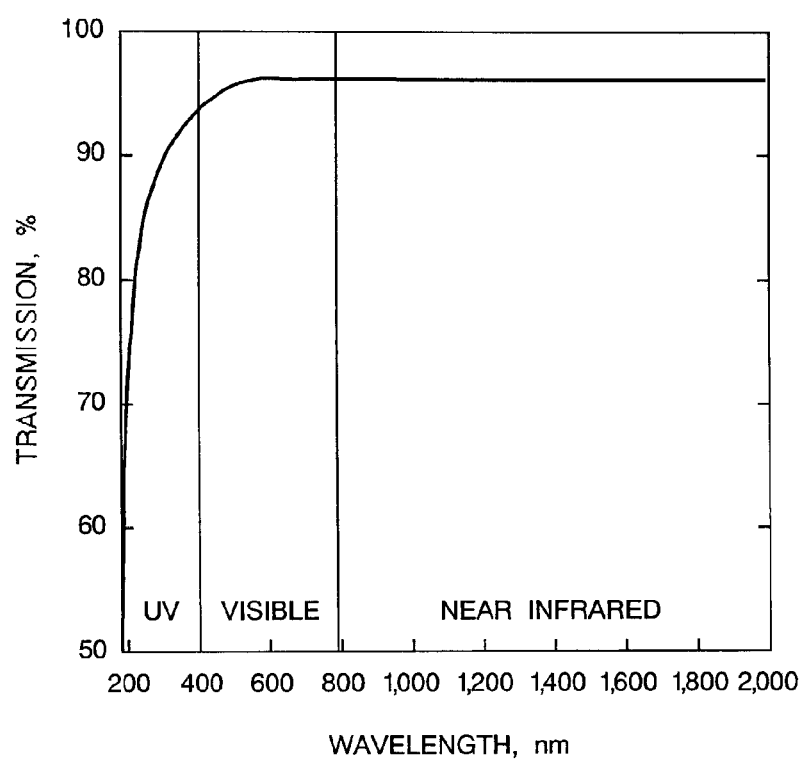
FIG. 20 is a graph showing the relationship between the F polymer transmission wavelength, and transmission percentage.

FIG. 20 is a graph showing the F polymer transmission spectrum. From this drawing, it is apparent that the F polymer 60 is suited for use as a filling medium since it does not absorb the fluorescent light of the argon laser having a wavelength of 488.0 nm and 514.5 nm, and it does not emit fluorescent light even if this light is irradiated.

FIG. 22 shows the refractive index of the F polymer and F' polymer. The refractive index of F polymer at a temperature of 20° C. according to sodium D ray is 1.29, and that of F' polymer at a temperature of 20° C. according to sodium D ray is 1.32.

The refractive index has been measured by an ABB reflection measuring instrument using alpha-bromonaphthalene as a contact liquid. This refractive index is known to be the lowest value for the solid organic polymer. The refractive index of the AF2400 is close to the theoretical minimum critical value of the solid organic polymer refractive index expounded by Groh and Zimmerm.

As described above, when the space between capillaries is filled with the fluorine containing polymer having a refractive index from 1.25 to 1.32, for example, 1.29, it is possible to avoid loss of light intensity due to the refraction and reflection caused when laser beams 24 and 25 pass through the surface of the fused silica tube 18. Almost the same signal as that of embodiment 1 can be obtained.

Embodiment 4

Figure 9A:
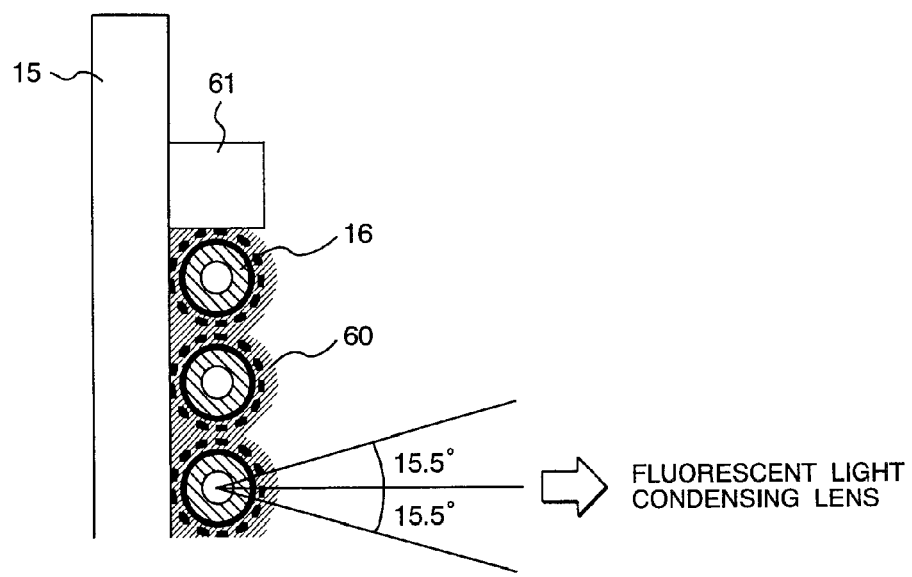
FIG. 9 includes a side view representing a portion of a multi-capillary array including the irradiatable portion according to embodiment 4 described below, and a side view representing a portion of a multi-capillary array including the irradiatable portion according to embodiment 3 described below.

FIG. 9a is a side view representing the portion close to the laser-irradiation part according to an embodiment 4. In this embodiment, the surface of the filled F polymer 60 is configured in such a way that the cross section forms a circle concentric with the capillary 16, as shown in FIG. 9a. Otherwise, the configuration is the same as that of embodiment 3.

Figure 9B:
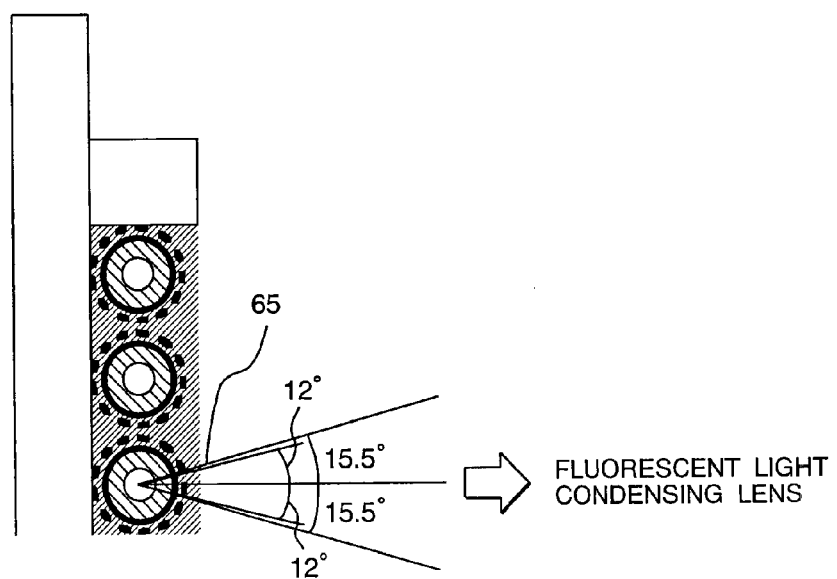

In embodiment 4, the fluorescent light collimating lens 31 is assumed to have an F value of 1.8. When the surface of the F polymer 60 has a plane surface (FIG. 9b), the signal is refracted by the boundary 65 between air and F polymer 60.

Accordingly, only the signal light within ±12° in the capillary cross section can reach the fluorescent light collimating lens 31, as illustrated. In the meantime, if the surface of the F polymer 60 is designed as a circle concentric as that of the capillaries 16, then the signal light within ±15.5° in the capillary cross section can reach the fluorescent light-collimating lens 31. When fluorescent light emitted from the test sample in the capillary passes through the boundary between the fused silica tube and F polymer 60, and the boundary between the F polymer and outside air, the fluorescent light enters the plane normal to these boundaries. Consequently, the fluorescent light does not refract, so there is no problem caused by aberration. As described above, the surface of the filled F polymer 60 is molded so that the cross section forms part of the circle concentric to that of the capillary, whereby the intensity of fluorescent light detected by the measuring part (CCD 34) is increased, with the result that sensitivity is improved.

The resolution is also improved by molding the filled F polymer 60 in such a way that the surface thereof has a predetermined curved surface. For example, a curved surface is formed in such a way that one cross section has a predetermined curve (an ellipse, hyperbolic curve, or circle where the central axis is different from that of the capillary). This allows the F polymer 60 to work as a lens so that a greater amount of fluorescent light emitted from the test sample can be focused onto the measuring part 34-3. It should be noted that the problem raised by aberration can be solved by forming the surface as a non-spherical lens or by providing the inspection part 34-3 with a filter.

As described above, the surface of the polymer 60 is formed to have a predetermined curved surface, and the forward direction of the fluorescent light is controlled so that the intensity of the fluorescent light entering the detection part is increased, whereby sensitivity can be improved.

Embodiment 5

Figure 10:
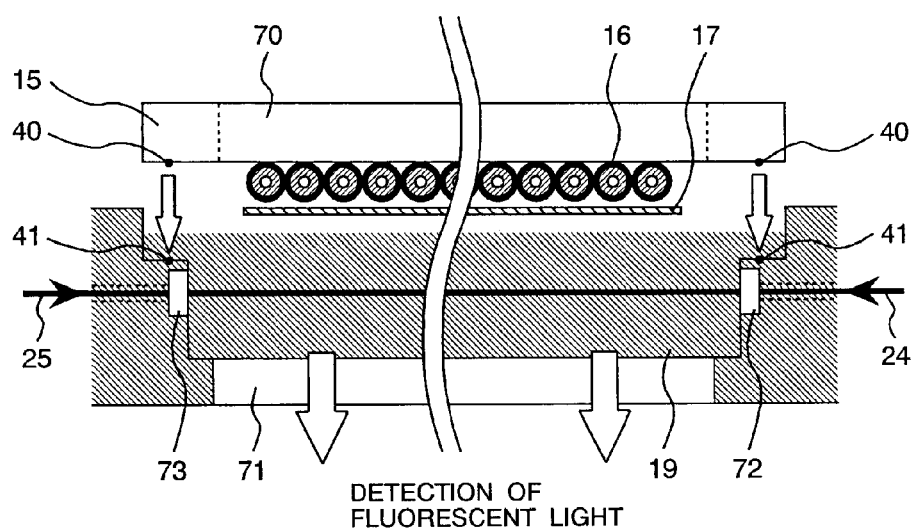
FIG. 10 is a side view representing a portion of a multi-capillary array including the irradiatable portion according to embodiment 5 described below.

FIG. 10 is a side view representing a portion of a multi-capillary array including the irradiatable portions of capillaries of the array, according to an embodiment 5. In embodiment 5, the liquid filling the space between capillaries exposed to the laser beam is not included in the cell structure of the capillary array. It is held by the cell structure that contains the liquid provided on the side of the capillary array electrophoresis apparatus proper. In this case, the capillary is dipped in the cell of the apparatus and the capillary is fixed in position. Other features not described in particular are the same as those in embodiment 1.

Except that the capillary array does not have a cell structure, the basic configuration of the irradiation part formed on the array base 15 is the same as that of embodiment 1. Capillaries are arranged on the array base 15 to ensure that all the capillaries 16 will contact the array base 15 and the adjacent capillaries, and are bonded and fixed to the array base 15 together with the holding plate.

The capillary array mounting section of the electrophoresis apparatus comprises a cell as a vessel to be filled with the F solution, fused silica windows 72 and 73 of the cell as irradiation parts passed by laser beams, a fused silica window 71 on the lower part of the cell as a fluorescent light transmission part, and a mounting reference surface 41.

The electrophoresis apparatus is configured so that the capillary array is mounted to face downward. The relative position between the array base 15 and electrophoresis apparatus can be adjusted by bringing the surface 40 of the array base 15 in contact with the mounting reference surface 41.

The cell of the electrophoresis apparatus is filled with the F solution 19, and laser beams 24 and 25 travel in the F solution 19 in the horizontal direction through the fused silica windows 72 and 73 of the cell. The capillary emits light downward, which is detected by the same detection part as that of the embodiment 1 through the fused silica window 71 on the lower portion of the cell.

To prevent the bubble from entering the laser light path, the array base 15 is provided with a hole 70. The hole 70 can be defined as formation of a hole through the array base 15. A similar effect can be achieved by forming a groove on the array base 15 positioned above the irradiation part. This allows the bubble in the vicinity of the irradiation part of the capillary to move upward, with the result that the bubble does not remain on the laser light path. In this embodiment, the irradiation part of the multi-capillary array is immersed in the F solution, so almost the same result of measurement as that in embodiment 1 can be achieved, with the result that the sensitivity of the electrophoresis apparatus can be improved.

Embodiment 6

In the embodiment 6, a polarizer element which transmits only laser light polarized in a direction and a half-wave plate element for rotating the polarization direction of the laser beam are properly arranged in an electrophoresis apparatus where laser beams are irradiated from both sides of multiple capillaries, thereby avoiding or suppressing the problem of laser oscillation being made unstable by the laser light returning to the laser oscillator.

Figure 11:
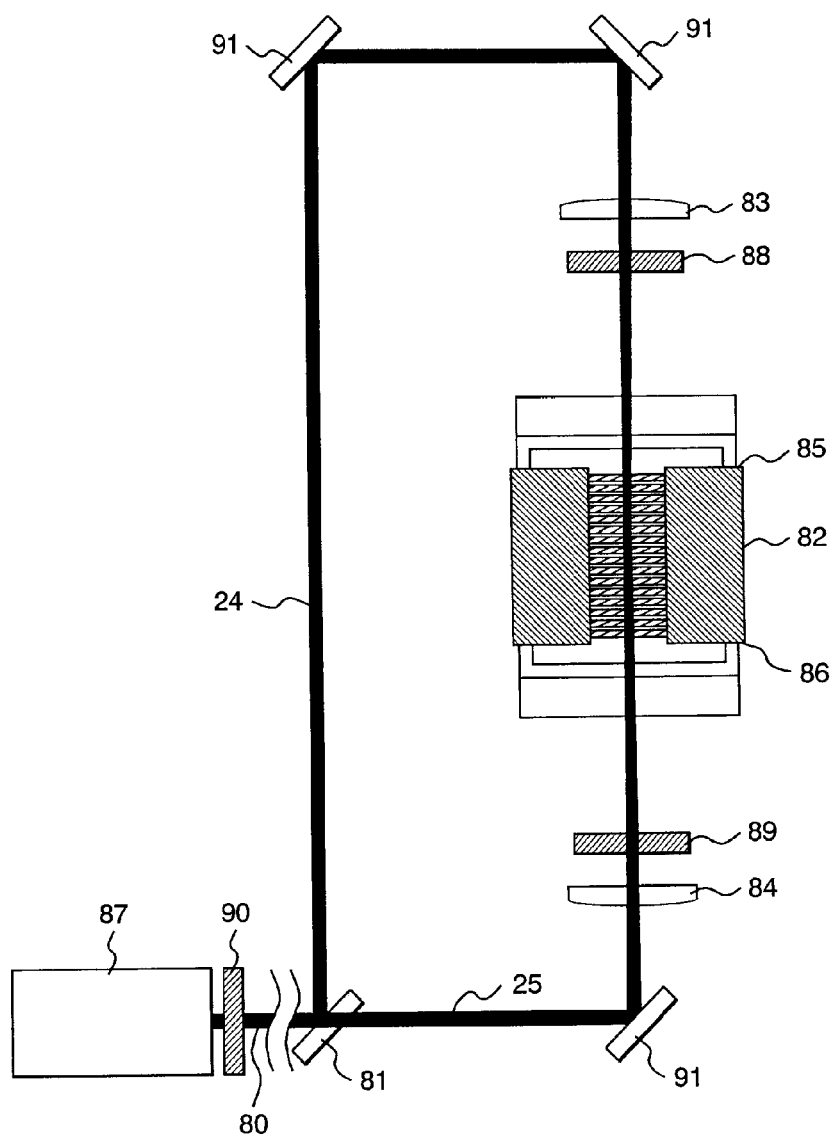
FIG. 11 is a schematic diagram representing the electrophoretic apparatus of embodiment 6 described below.

FIG. 11 is a schematic diagram representing the embodiment 6. The capillary array is configured in the same manner as that in embodiment 1. It indicates only the vicinity of the capillary array including the irradiatable part and laser light path, not the laser shutter or filter. The multi-capillary array electrophoresis apparatus according to the present embodiment comprises a capillary array having the same configuration as embodiment 1, an irradiatable part for applying two bundles of laser beams propagating multiple capillaries and adjusting the traveling direction of these two bundles of laser beams so as to make them opposite to each other, and a light cut-off part for ensuring that the laser beams having passed through the capillary array do not return to the laser properly.

The light cut-off part comprises a laser 87 as a light source for applying a laser beam 80 as coherent light, a half-mirror or beam splitter 81 capable of splitting one bundle of laser beams 80 into two equal parts to create two bundles of laser beams 24 and 25, a mirrors 91 for changing the traveling direction of laser light, and condensing lenses 83 and 84. The mirror, half-mirror or lens may be interposed in the path of the laser light. Alternatively, two separate laser light sources can be used instead of the beam splitter.

The light blocking part consists of half wave plates 88 and 89 ($\lambda/2$ plate, mica wave plate, etc.) as an element capable of changing the polarization direction of the transmitting light) and a polarizer 90 capable of transmitting only a predetermined polarized beam.

The laser beam 80 launched by the laser 87 is split into two substantially equal parts by the half mirror 81. These two laser beam s are introduced to the capillary array 82 from both sides of capillary array, where light reflected by the half mirror 81 is a laser beam 24, while the transmitted light is a beam 25. The condensing lens of the laser beam 24 is a condensing lens 83, while the condensing lens of the laser beam 25 is a condensing lens 84. Hereafter the capillary located at the end of the array where laser beam 24 is introduced will be called the first capillary 85, and the capillary where laser beam 25 is introduced will be called the 96th capillary 86.

The laser beams 24 and 25 are located in a plane surface (hereinafter abbreviated as "array surface") including the center axis of each of 96 capillaries and are introduced perpendicularly to the capillary. Laser beams 24 and 25 are coaxial to each other. The optical axis has been adjusted to ensure that one of them having passed through the capillary passed coaxially with the other incident laser beam to go back the laser 87.

Laser beams 24 and 25 are originally straight polarized beams, and their direction of polarization is vertical to the capillary axis when the half-wave plate and the polarizer are not placed along the laser beam excitation light paths. In the aforementioned configuration, the light reflected from the capillary array or the light having transmitted through the capillary array returns to the laser, causing such a problems as unstable laser oscillation and fluctuation of signal base line. When the halfwave plate and the polarizer are not used, each of the intensities of the transmitted light returning and that of the reflected light returning is about 6 percent of the incident light intensity, respectively.

To minimize this returned light, half wave plates 88 and 89 such as a crystal λ/2 plate or mica wave plate were placed as an elements for rotating polarization direction on the capillary side of the laser condensing lens for laser beams 24 and 25 from both upper and lower directions. The sequence of the optics in the order of the laser beams beam paths can be the laser, the half-mirror, the polarizer, the condensing lens, the half-wave plate, and the capillary array. In cases where two laser beams are used to irradiate respective sides of a capillary array, two 10 polarizers and two half-wave plates can be used along with a single polarizer.

According to various embodiments, the installation of the polarizing filter and polarization rotating element is not limited to the above-mentioned installation. For example, according to various embodiments both the polarizing filter and the polarization rotating element can be installed on the capillary side of the branching point. In this case, two each of the respective optical elements can be used. The polarization rotating element can be installed on the laser side of the branching point. In this case, a single polarization rotating element is required.

The sequence of the condensing lens and the half-wave plate can be exchangeable. The rotation angles of the polarizer and the half-wave plate around the optical axis can be adjusted as follows:

The rotation angle of the half-wave plate can be adjusted so that the angle of rotation for polarization will be 45° to the capillary axis and the polarization direction for the two incident laser beam is 90°. The angle of the polarizer can be adjusted in such a way that the intensity of the transmitted light from the laser through the half-wave plate can be maximized.

The polarization direction of the incident light can be turned an additional 45° by passing through the second half-wave plate after propagating the capillary array. Because the total rotation angle is 90°, the laser beams that propagate the capillary array and the two half-wave plates can be blocked by the polarizer before those beams get back to the laser oscillator. It should be noted that the rotation angle of the half-wave plate and polarizing direction of the polarizer is not strictly limited to the aforementioned figures, but large tolerance is allowed if the intensity of returned light is suppressed to a level that does not cause laser unstabilization.

In the present embodiment, the half-wave plate can be arranged on the capillary array side rather than on the split point, and the polarizer can be arranged on the laser side rather than on the split point. The polarizer placed in the vicinity of the laser has its angle adjusted to ensure that the intensity of laser light at the position of capillary array is maximized. The light that has come back along the loop-formed light path after passing through the capillary array has its direction of polarization turned 90°. As a result, the intensity of the transmitted light of the polarizer is suppressed for the returned light.

The arrangement of the polarizer and the half-wave plate is not restricted to the aforementioned one. For example, both the polarizer and the half-wave plate may be placed on the capillary side rather than on the split side. In this case, two of each of the respective optical elements can be used. Further, the polarizer can be placed on the laser side rather than on the split side. In this case, only one polarizer is needed. In this manner, the laser beam launching from the laser 87 properly passes through the polarizer (angle adjusted to maximize the transmitted light) and is split into two parts by the half mirror. After having passed through the half-wave plate, laser light is introduced to the capillary array from two directions. The polarized light of the laser vertical to the capillary axis is turned 45° by the half wave plate 88, and enters the capillary array at an angle of 45° with respect to the capillary axis. On the aforementioned light path, the polarizing direction of the two upper and lower laser beams can be vertical to each other at the point of the capillary array. The intensity of the signal light from inside the capillary depends on the polarization direction of the incident laser beams but two upper and lower laser beam bundles have angles of 45° with respect to the capillary axes, so the intensity of the signal light of 96 capillaries is distributed with symmetrical upper and lower parts.

Laser light having propagated the capillary array passes through the half-wave plate (polarized light turned in the same direction as the first half-wave plate). The half-wave plates arranged on both sides of the capillary array are set to rotate the polarization direction of the laser light in the same direction. So the laser light emitted from one end of the capillary passes through the capillary; then the direction of polarization is turned again by the half-wave plate, and is oriented substantially perpendicular to the initial polarization direction of the laser light.

Then the light enters the polarizer via the half mirror. Here the second polarizer is the same as that of the first polarization filter. The returned light enters from the opposite direction. However, the polarization direction of return light is turned 90°. In other words, the polarized light of the laser beams 24 in the direction vertical to the capillary axis is turned 45° by the half wave plate 88, and enters the capillary array with the polarization direction being at an angle of 45° to the capillary axis. After laser beams 24 have passed through 96 capillaries, the polarization of the beams is turned a further 45° by the half wave plate 89. The laser beams 24 have a polarization direction turned a total of 90° by passing through the two half wave plates 88 and 89. Similarly, the transmitted light of laser beam 25 has its polarization direction turned by 90°. The transmission light enters the polarizer. The angle of this polarizer can be adjusted to maximize the intensity of light coming from laser side, and the light on its way of returning to the light path through the capillary array has its polarization direction turned by 90°. So the polarizer is adjusted so that the intensity of the transmitted light having returned will be minimized.

Consequently, it cannot pass through this polarizer and cannot reach the laser head in a large amount. This prevents the returned light from reaching the laser. In the step of passing through the 96 capillaries, the linearly polarized light is disturbed and the linearly polarized components are reduced about 25 percent compared to the one before passing through the capillaries. However, the present invention has succeeded in reducing the return of transmitted light by 75 percent.

The present embodiment solves the problem where the light having passed the capillary array returns to the laser oscillator to deteriorate laser oscillation stability, and provides relatively stable laser oscillation

Embodiment 7

According to various embodiments, the angle of laser light entering the capillary can be made non-vertical or non-perpendicular to the multi-capillary array. This angling can be included in electrophoresis apparatus where excitation is directed at the array from one or both sides of the array.

Figure 12:
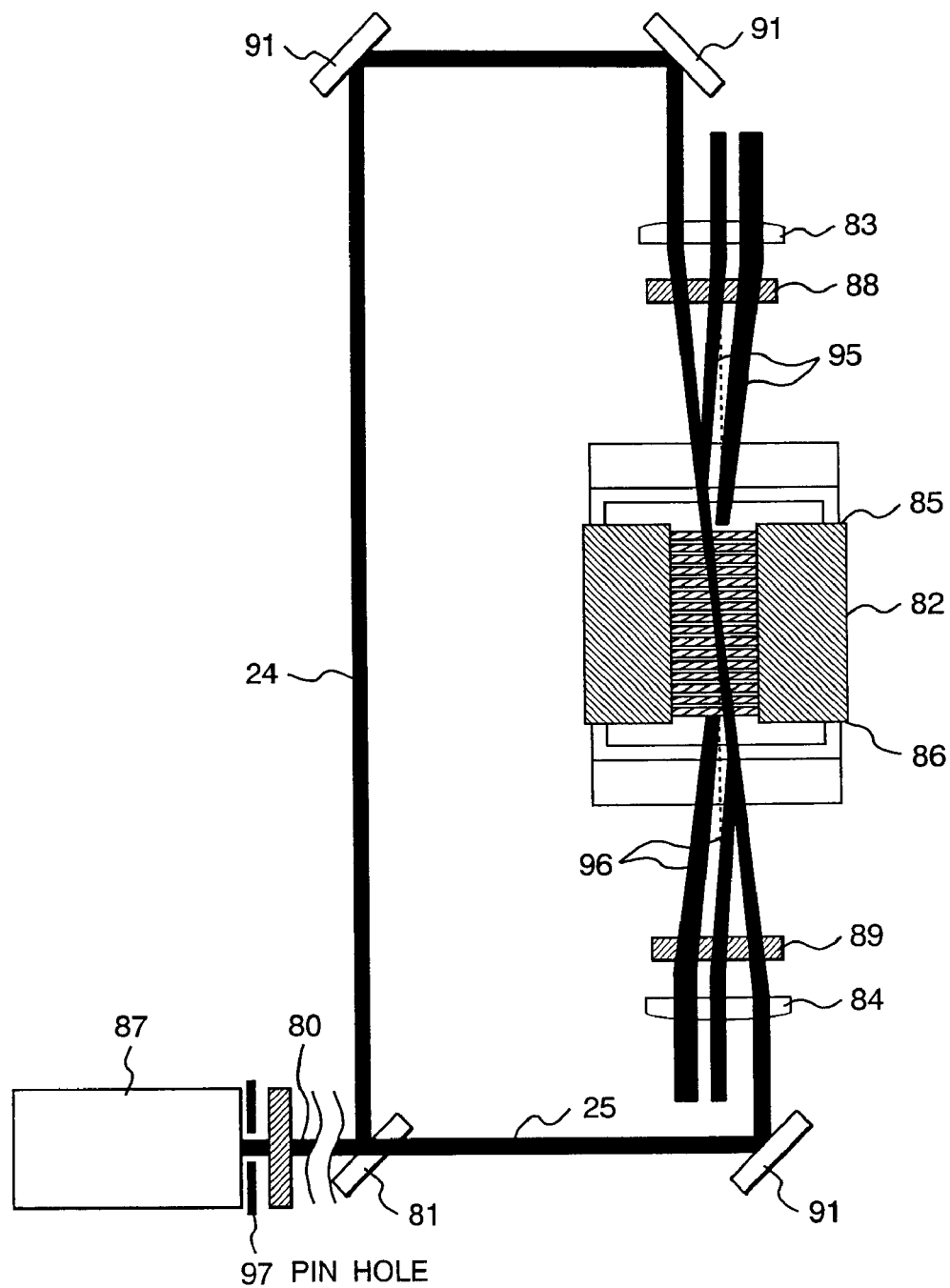
FIG. 12 is a schematic diagram representing the electrophoretic apparatus of embodiment 7 described below.

FIG. 12 is a schematic view of the embodiment 7. The configuration of this embodiment is basically the same as that of the embodiment 6, except for the optical axis of the irradiation part. However, the laser light is introduced into the aforementioned irradiatable portion at an angle of about 2° deviated from normal with respect to the axial lengths of the irradiatable portions of the capillaries. Further, a pinhole plate 97 can be provided as a light selection member. This light selection member comprises an opening that allows transmission of the laser light traveling from the light source to the capillary, and a partition for blocking of the returned laser light traveling from the capillary to the light source.

Laser beams 24 and 25, which can also be referred to herein as laser beam bundles, are propagated the array surface, and enter the capillary at an angle 2° deviated from the normal. Laser beams 24 and 25 can be coaxial with each other when they irradiate the capillary array. The optical axis of the beams can be adjusted in such a way that one of the laser beams that passes through the capillary travels coaxially with the other laser beam, and goes back to the laser 87. As a result, the beams 95 and 96 reflected from the capillary or cell by laser beam s 24 and 25 travel along optical axes different from the optical axes of the incident lasers shown in FIG. 12.

A pinhole plate 97 having a 1.4 mm-diameter pinhole as a light selection means that does not interfere with the laser beam coming from laser side and, at the same time, that does not transmit the laser light reflected from the capillary, can be installed at a position close to the laser outlet. The laser light from the laser 87 passes through the pinhole, but the reflected light cannot pass through it. This makes it possible to prevent the reflected beams 95 and 96 from returning to the laser oscillator 87. Consequently, this solves the problem of the light reflected from the capillary and cell returning to the laser oscillator to cause instability of laser oscillation.

When this embodiment is combined with embodiment 6, the return of the transmitted light is reduced and according to the method of embodiment 6, return of the reflected light is reduced according to the method of the present embodiment, whereby stable laser oscillation can be ensured.

Embodiment 8

According to present embodiment 8, the filling medium applied around the capillary can be formed into a predetermined curved surface, to ensure that fluorescent light emitted from the capillary is not diverged when passing through the boundary of the filling medium.

Figure 16A:
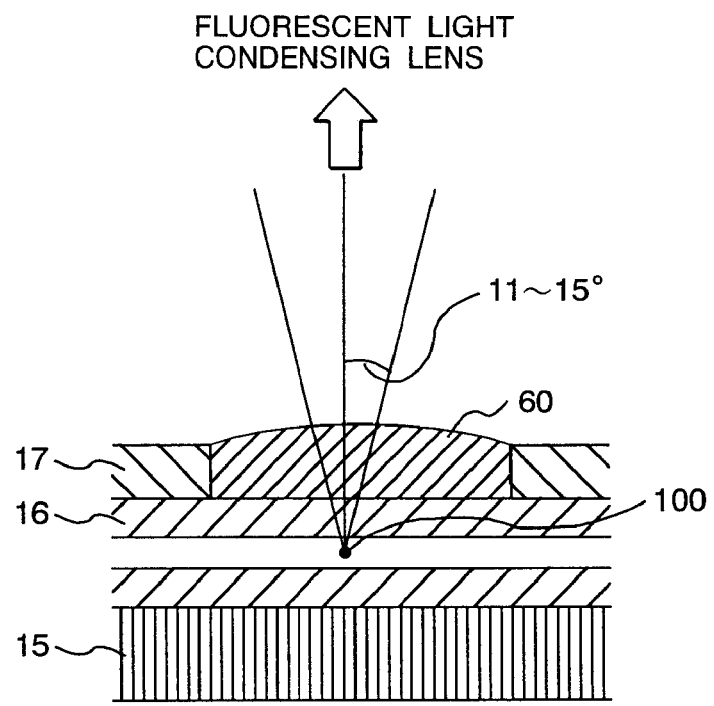
FIG. 16 includes schematic drawings representing the light-gathering lenses of embodiment 8 described below.
Figure 16B:
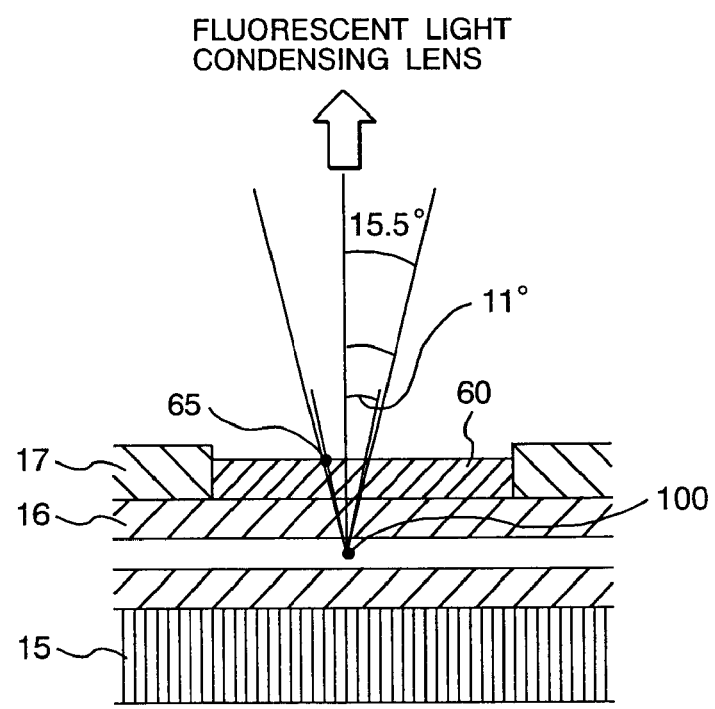

FIG. 16 is a top view of an array portion showing an irradiatable portion of a capillary according to embodiment 8. Otherwise, the configuration is the same as that of the embodiment 3. As shown in FIG. 16 (a), the F polymer 60 as a filled medium is formed to have a convex surface as viewed from the laser irradiation part 100 in the capillary. Here the "f#" of the fluorescent light collimating lens 31 is 1.8. If the F polymer 60 has a plain surface ("b" in FIG. 16), signal light will refract on the boundary 65 between air and F polymer 60, so only signal light within about ±11° on the cross section of the capillary can reach the fluorescent light collimating lens 31, as illustrated.

In the meantime, if the F polymer 60 has a convex surface ("a" in FIG. 16), signal light within about ±11° to 15° on the cross section of the capillary reaches the fluorescent light-collimating lens, depending on the curvature radius of the surface. As described above, the intensity of the fluorescent light coming from the capillary 16 can be increased by forming the filled F polymer 60 to have a curved convex surface.

To ensure an effective increase of the intensity of the fluorescent light, the center of the convex on the surface of the F polymer 60 can be aligned with the laser light axis. Since the fluorescent light emitted from the test sample travels in the direction vertical to the convex surface of the F polymer 60, there is no change in the traveling direction when passing through the convex surface (boundary surface). This also reduces the problem of aberrations at the CCD.

The sensitivity can also be improved by forming the surface of the filled F polymer 60 into a predetermined curve. For example, a curved surface is configured in such a way that a cross-section is shaped in a predetermined curve (an ellipse, hyperbola, or circle whose center is different from the laser light path). This allows a greater amount of fluorescent light to be converged by the CCD camera as a detection part, with a resultant increase in the intensity of the fluorescent light detected by the CCD. In other words, the F polymer 60 will work as a lens and the traveling direction of the fluorescent light can be adjusted by forming the surface of the F polymer 60 around the capillary to have a predetermined curve. It should be noted that the problem of aberrations can be solved by forming such a lens to have multiple focuses on the surface of the F polymer 60.

The surface of the F polymer 60 is not restricted to one in contact with air. It can refer to the surface in contact with the medium having a refractive index different from that of the F polymer 60. Another medium having a different refractive index can be present between the F polymer and capillary. This embodiment can be implemented simultaneously with embodiment 4.

Embodiment 9

Embodiment 9 provides a method for forming a predetermined curved surface of the outer mold of a vessel covering the filling medium around the capillary, thereby ensuring that the fluorescent light emitted from the capillary will not be diverged when passing through the surface of the vessel.

Figure 17A:
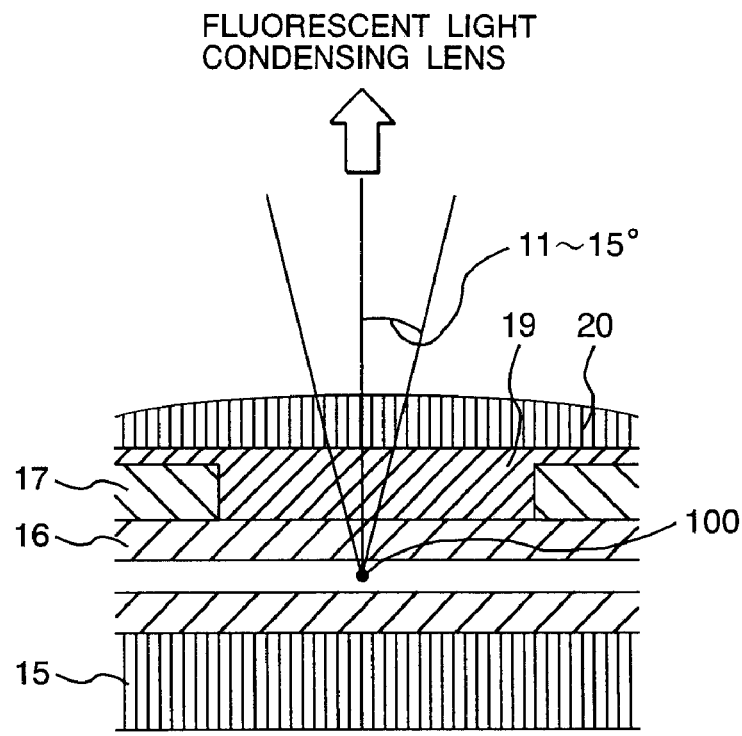
FIG. 17 includes schematic drawings representing the light-gathering lenses of embodiment 9 described below.
Figure 17B:
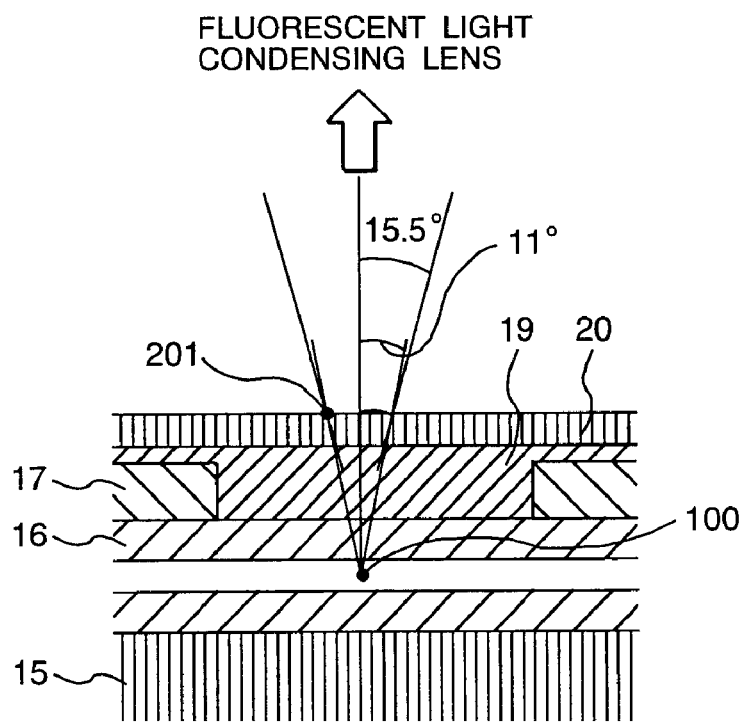

FIG. 17 is a top view representing the portion close to the irradiation part according to embodiment 9. Otherwise, the configuration is the same as that of embodiment 1. As shown in FIG. 17a, the surface of the cell cover 20 is convex, as viewed from the laser-irradiation part 100 in the capillary. Assume that the "f#" of the fluorescent light condensing lens 31 is 1.8. When the surface of the cell cover 20 has a plane surface (FIG. 17b), signal light is refracted by the boundary 101 between air and cell cover 20, so only the signal light within the range of about ±11° on the cross-section of the capillary reaches the fluorescent light collimating lens 31, as illustrated.

When the cell cover 20 has a convex surface as shown in FIG. 17a, the signal light within the range of about 11° to 15° on the capillary cross-section reaches the fluorescent light collimating lens, depending on the curvature radius of the surface profile.

As described above, it is possible to increase the intensity of the fluorescent light from the capillaries 16 to be detected by forming the cell cover 20 to have a convex surface. To ensure an effective increase of the intensity of the fluorescent light, the center of the circular arc of the convex on the surface should preferably be aligned with the laser light axis. Further, fluorescent light can be converged by the CCD camera as a detection part and the intensity of the fluorescent light can be increased by forming the curved surface of the cell cover to have a smaller curvature radius. In other words, a vessel with a cell cover will work as a lens and the traveling direction of the fluorescent light can be adjusted by forming the surface of the vessel with the cell cover to have a predetermined curve.

The surface of the cell cover is not restricted to the one in contact with air. It can refer to the surface in contact with the medium having a refractive index different from that of the vessel with the cell cover. Another medium having a different refractive index can be present between the cell cover and the filling medium forming the boundary.

Embodiment 10

According to embodiment 10, a multi-capillary array having a planar surface can be provided with a cylindrical lens where one side is planar and the other side is curved, whereby the function of the convex surface of the cell cover in embodiment 9 is performed by the cylindrical lens 102 mounted on the apparatus.

Figure 18:
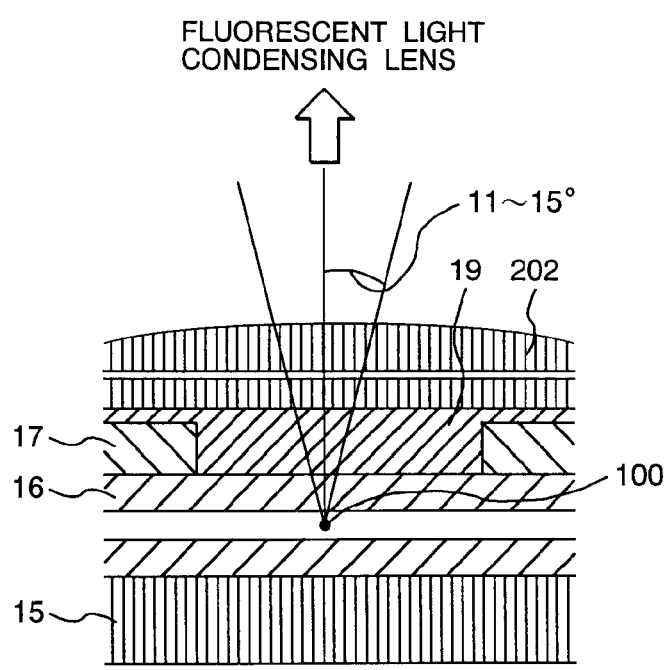
FIG. 18 is a schematic drawing representing the light-gathering lens of embodiment 10 described below.

FIG. 18 is a top view representing the portion close to the laser-irradiatable part of embodiment 10. In this embodiment, the cylindrical lens 202 mounted on the electrophoresis apparatus properly covers the cell cover of the multi-capillary array according to the present embodiment 1. Otherwise, the configuration is the same as that of the embodiment 1.

The function of the convex surface in the embodiment 9 can be performed by the cylindrical lens 202 mounted on the apparatus, so a glass plate with plane surface can be used as the cell cover of the capillary array as a consumable component. Further, since the cylindrical lens 202 is mounted on the apparatus, the center of the convex surface of the cylindrical lens 202 is aligned with the laser light axis. This provides an advantage that the intensity of the laser beams does not depend on the capillary array mounting accuracy.

Embodiment 11

FIG. 19 contains a front view (19a) representing a portion of a multi-capillary array including the laser irradiatable part and a cross-sectional view (FIG. 19b) taken along line A-A' of the front view of FIG. 19 a. In this embodiment, a background light shielding or blocking member having a detection window allowing passage of the fluorescent light emitted from the sample in a capillary is arranged over the capillaries placed in parallel on the fused silica-made array base 15 for the irradiatable portion. Otherwise, the configuration is the same as that of embodiment 1.

All the 96 capillaries 16 are arranged on the array base 15 and are bonded and fixed on the array base 15 together with the silicon plate 101. A detection window partitioned by a protective guard 102 and a V-groove 104 for positioning the capillaries 16 are formed on the silicon plate 101 by silicon anisotropic etching technology. Since the capillaries 16 fit in the V groove, they can be arranged at a predetermined interval with a high degree of precision, and the detection window 103 partitioned by the protective guard 102 and the capillary 16 can be easily positioned.

Further, a silicon plate-positioning guide 105 is formed on the array base 15. This is within the permissible detection range of the measuring part. In other words, if all the capillaries 16 are located inside the silicon plate-positioning guide 105, all the capillaries 16 will be within the permissible detection range of the detection part. The capillary 16 and array base 15 can be easily positioned with each other by the silicon plate positioning guide 105 formed on the array base 15.

The capillaries 16 can be configured in such a way that the fused silica tube 18 can have an inner diameter of 50 μm and an outer diameter of 126 μm covered with a 12 μm thick polymer coating. The total outer diameter can be 150 μm. The capillaries can be filled with an aqueous polymer solution (refractive index: 1.41) as a DNA separation medium. In the irradiation part, the polymer coating can be removed, and the fused silica tube 18 can be exposed.

When exposed to laser light, part of the irregularly reflected laser light irradiates the polymer coating of the capillary 16 to produce fluorescent light, or the part of the fluorescent light emitted by the DNA sample is irregularly reflected. When the fluorescent light from the polymer coating and the light irregularly reflected from the DNA sample are received, the signal to noise ratio will be reduced due to increase of the background light, with the result that detection accuracy is deteriorated.

However, the desired laser beam passes through the detection window 103, but the background light is cut off by the silicon plate, whereby the increase of background light can be avoided. Further, to ensure that the light reflected from the array base 15 does not pass through the detection window 103 and is not received by the detection part, a reflection preventive film 106 is formed on the array base 15. This further reduces the background light, so the detection accuracy can be further improved.

The irradiatable portions of the capillaries can be surrounded by F solution 19. The F solution 19 can be completely sealed by the fused silica-made cell cover 20, array base 15, and adhesive for bonding them together. To prevent the cell sealing structure from being damaged by the volume expansion of the F solution 19 resulting from temperature change, the sealing structure can contain a highly compressible foam 107 having a foaming magnitude of 30 times (foam accounting for about $^{29}\!/_{30}$th of the total volume). The volume expansion of the F solution 19 is 0.0012 mm$^3$/mm$^{3\circ}$ C. If the difference between the capillary array storage temperature (room temperature: 25° C.) and working temperature (60° C.) is assumed as 35° C., then increase in volume resulting from temperature rise (35° C.) of the F solution 19 from the storage temperature to working temperature is about 0.04 mm$^3$/mm$^3$ (about 4%). The size of the foam 107 is assumed to be about 10 percent of the cell volume.

The foam 107 can be arranged in the groove formed on the array base 15 so that it is sandwiched between the array base 15 and capillaries 16. Further, the foam 107 can be excited by scattered excitation light, but is placed at a hidden position by the silicon plate 101. This avoids increase of the background light due to the fluorescent light from the foam 107. Further, the foam 107 can be placed in a hole 109 for pouring the F solution in the sealed part of the cell as a cover to block the hole. This eliminates the need of special processing only for the foam 107 on the array base 15.

To prevent bubbles from entering the laser light path, absence of bubbles inside the cell can be ensured, but it is not easy to eliminate bubbles completely. Even if a bubble has entered the cell filled with F solution, the fused silica-made bubble-eliminating block 23 is formed in the cell in order to ensure that the bundle prevents the bubble from entering the laser light path.

To maintain constant the angle between the incident laser beam and the laser incident surface of the cell, a guide 108 can be used as a cell cover-positioning groove formed on the array base 15. This ensures easy and reliable positioning on the array base 15. This configuration provides a capillary array having a high signal to noise ratio and reduced background light.

LEGEND OF THE REFERENCE SIGNS IN THE DRAWINGS

1. Capillary array, 2. Negative electrode, 3. Buffer on negative electrode side, 4. Gel block, 5. Connection to a gel block, 6. Valve, 7. Ground electrode, 8. Irradiatable portion or part, 9. Laser beam, 10. Syringe, 11. Air-circulating oven, 11-1. Light source, 11-2. High voltage power source, 11-3. Sample introduction part, 11-4. First buffer vessel, 11-5, Fluid medium injection part, 11-7. Second buffer 11-6. Detection part, 12. Buffer on ground electrode, 15. Array base, 16. capillary, 17. capillary holding plate, 18. fused silica tube, 19. 3M-made fluorine solution containing "Fluorinert" FC43 for filling the space around the capillaries, 20. Quartz-made cell cover, 20-2. Bubble storage space, 21. Adhesive for fixing the cell cover, array base and capillary in position, 22. Bubble, 23. Fused silica-made bubble eliminating block for preventing bubbles from entering the laser light path, 24. and 25. Laser beams, 31. Fluorescent light collimating lens, 32. Grating, 33. Focus lens, 34. CCD, 34-2. Detecting mechanism, 35. Emission from capillary, 36. Luminous flux formed of light emitted from the capillary converted into parallel light by a fluorescent light collimating lens, 40. Reference surface P for array base, 15,40-2. Reference plane surfaces for arranging the capillary array, 41. Mounting reference surface P' on the array irradiatable portion or part mounting section, 44. Holding rod, 45. Spring, 46. Reference surface Q vertical to the surface P of the array base and parallel to the X-axis, 47. and 48. Mounting reference lines in contact with reference surface Q of the array base on the array irradiatable portion or part mounting section, 50. Surface R of the fused silica surface of cell cover passed by laser light, 51. Surface S of the quartz surface of cell passed by laser light, 51-6. Excited light transmission part, 51-7. Laser beam transmission part, 51-8. Pressure part A, 51-9. Pressure part B, 51-10. Spring, 51-11. Mounting section cover, 52. Surface T of the fused silica surface of cell passed by laser light, 53. Surface Y of the quartz surface of cell passed by laser light, 54. A point of the portion in contact with F solution of the array, 55. A point of the portion in contact with F solution of the cell cover, 60. Fluorinated polymer for covering the irradiation part of capillary array, 60-2. Irradiatable portion or part, 61. and 62. Polymer block located outside the capillaries on both ends to intercept fluorinated polymer, 65. Boundary between air and F polymer 60, 70. Drilled hole on the array base for preventing entry of bubbles on the laser light path, 71. Quartz window for detecting fluorescent light on the bottom of the cell, 72. and 73. fused silica windows for laser beam transmission, 80. Laser beam, 81. Half mirror, 82. Capillary array, 83. and 84. Laser light condensing lens, 85. and 86. End capillary passed by laser beam, 87. Laser, 88. and 89. Half wave plates, 90. Polarization filter, 91. Mirror, 95. and 96. Laser beams reflected by capillary and cell, 97. Pinhole plate, 101. Silicon plate, 102. Protective guard, 103. Detection window, 104. V-groove, 105. Silicon plate positioning guide, 106. Reflection preventive film, 107. Foam, 108. Cell cover positioning guide, 109. F solution injection hole, 202. cylindrical lens.

What is claimed is:

1. A device comprising:
    a multi-capillary array including a plurality of capillaries arranged in a row on a plane and filled with a separation medium, each capillary of the plurality having a respective first portion for introducing a sample, and a respective light-irradiatable portion capable of being irradiated with excitation light, wherein the plurality of capillaries of the multi-capillary array are arranged side by side, and are in contact with each other;
    a first source of first excitation light beams, disposed in a position to emit the first excitation light beams in a first direction along a first excitation light beam path substantially perpendicular to a first side of the row of the plurality of capillaries;
    a polarizing plate disposed in the first excitation light beam path between the first source and the multi-capillary array;
    a second source of second excitation light beams, disposed in a position to emit the second excitation light beams in a second direction along a second excitation light beam path that is substantially opposite to the first direction and substantially perpendicular to a second side of the row of the plurality of capillaries, and wherein the polarizing plate is disposed in the second excitation light beam path between the second source and the multi-capillary array, and wherein the first side is different than the second side;
    a first half-wave plate for transmitting first reflected light reflected from a first surface of the capillaries in a first reflected direction, not aligned with said first excitation light beam path, so as to prevent the first reflected light from entering the first source, the first half-wave plate being disposed in the first excitation light beam path, between the multi-capillary array and the polarizing plate; and
    a second half-wave plate for transmitting second reflected light reflected from a second surface of the capillaries in a second reflected direction, not aligned with said second excitation light beam path, so as to prevent the second reflected light from entering the second source, the second half-wave plate being disposed in the second excitation light beam path, between the multi-capillary array and the polarizing plate.

2. The device according to claim 1, wherein the first source of first excitation light beams and the second source of the second excitation light beams comprise separate light sources.

3. The device according to claim 1, wherein the first source of first excitation light beams and the second source of second excitation light beams, comprise the same excitation light source, and a beam splitter is disposed along a beam path between the excitation light source and the multi-capillary array.

4. The device according to claim 3, wherein the excitation light source comprises a single laser excitation light source.

5. The device according to claim 3, wherein excitation light transmitted through the beam splitter is directed along a first beam path toward the multi-capillary array, and excitation light reflected by the beam splitter is directed along a second beam path toward the multi-capillary array, and wherein the first and second beam paths travel in directions substantially opposite to one another as they respectively pass through the multi-capillary array.

6. The device according to claim 1, wherein the first half-wave plate rotates the polarization of excitation light emitted from the first excitation light source, about 45°.

7. The device according to claim 1, further comprising a detector capable of detecting light emitted by samples in the light-irradiatable portions upon irradiation with excitation light, wherein the multi-capillary array further includes a barrier that blocks excitation light that is reflected by the light-irradiatable portions in a direction toward the detector.

8. A device comprising:
a multi-capillary array including a plurality of capillaries arranged in a row on a plane and filled with a separation medium, each capillary of the plurality having a respective first portion for introducing a sample, and a respective light-irradiatable portion capable of being irradiated with excitation light, wherein the plurality of capillaries are arranged side by side, and are in contact with each other;
a source of first and second excitation light beams, disposed in a position to emit the first excitation light beams in a first direction along a first beam path substantially perpendicular to a first side of the row of the plurality of capillaries, and to emit the second excitation light beams in a second direction, opposite to the first direction, along a second beam path substantially perpendicular to a second side of the row of the plurality of capillaries, the first side being different than the second side;
a polarizing plate disposed in the first and second excitation beam paths between the source and the multi-capillary array;
a first half-wave plate disposed between the multi-capillary array and the polarizing plate, and in the first beam path;
a second half-wave plate disposed between the multi-capillary array and the polarizing plate, and in the second beam path, wherein incident angles of the first and second excitation light beams toward the respective sides of the row of the plurality of capillaries are inclined.

9. The device according to claim 8, further comprising a pin-hole plate, for blocking transmitted returning reflected light.

10. The device according to claim 8, wherein an excitation light beam from the source is split by a beam splitter into the first and second beam paths.

* * * * *